US012806259B2

(12) United States Patent
Rooney et al.

(10) Patent No.: US 12,806,259 B2
(45) Date of Patent: Nov. 24, 2026

(54) PLATFORM FOR ACTIVATION AND EXPANSION OF VIRUS-SPECIFIC T-CELLS

(71) Applicant: Baylor College of Medicine, Houston, TX (US)

(72) Inventors: Cliona M. Rooney, Bellaire, TX (US); Natalia Lapteva Doyle, Houston, TX (US); Sandhya Sharma, Houston, TX (US); Dimitrios Wagner, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 343 days.

(21) Appl. No.: 17/661,060

(22) Filed: Apr. 28, 2022

(65) Prior Publication Data

US 2022/0251509 A1 Aug. 11, 2022

Related U.S. Application Data

(63) Continuation of application No. 16/331,494, filed as application No. PCT/US2017/051284 on Sep. 13, 2017, now abandoned.

(60) Provisional application No. 62/395,438, filed on Sep. 16, 2016.

(51) Int. Cl.

*A61K 40/11* (2025.01)
*A61K 39/12* (2006.01)
*A61K 40/42* (2025.01)
*A61K 40/46* (2025.01)
*C12N 5/0783* (2010.01)

(52) U.S. Cl.

CPC .............. *A61K 39/12* (2013.01); *A61K 40/11* (2025.01); *A61K 40/421* (2025.01); *A61K 40/46* (2025.01); *C12N 5/0638* (2013.01); *A61K 2239/48* (2023.05); *C12N 2501/2307* (2013.01); *C12N 2501/2315* (2013.01); *C12N 2710/16234* (2013.01); *C12N 2740/16034* (2013.01); *C12N 2760/16134* (2013.01); *Y02A 50/30* (2018.01)

(58) Field of Classification Search

None

See application file for complete search history.

(56) References Cited

U.S. PATENT DOCUMENTS 7,079,309 B1 7/2006 Lin et al.
9,963,677 B2 5/2018 Leen et al.
9,974,808 B2 5/2018 Bonini et al.
2011/0059133 A1* 3/2011 Adhikary ............. A61K 39/245 435/378
2012/0094865 A1 4/2012 Mallone et al.
2015/0017723 A1 1/2015 Rooney et al.
2016/0008398 A1 1/2016 Sadelain et al.
2018/0079824 A1* 3/2018 Ahmed ................ C12N 5/0636
2018/0125891 A1* 5/2018 O'Reilly ................ A61P 35/00
2021/0380943 A1* 12/2021 Bollard ................ C12N 5/0636
2022/0282218 A1* 9/2022 Leen ....................... A61P 31/16
2023/0383254 A1* 11/2023 Reisner ............. A61K 39/4611

FOREIGN PATENT DOCUMENTS

WO 2011/130249 A2 10/2011
WO 2013088114 A1 6/2013
WO 2015/066057 A2 5/2015
WO 2016/008398 A1 1/2016
WO 2016/044853 A1 3/2016
WO 2016/198480 A1 12/2016

OTHER PUBLICATIONS

De St. Groth et al. "T cell activation: in vivo veritas" Immunology and Cell Biology 2004, 82: 260-268.
Dotti etal. for example, Immunol Rev. 2014, 257(1)1-35.
Doubrovina et al ( Blood, 2012, v.119 pp. 2644-2656).
Hombach et al., "Superior Therapeutic Index in Lymphoma Therapy: CD30 CD34 Hemtopoietic Stem Cells Resist a Chimeric Antigen Receptor T-cell Attack," The American Society of Gene & Cell Therapy, Molecular Therapy, vol. 24, No. 8, Epub Aug. 2016, pp. 1423-1434.
Lam et al: "Developing Multi-HIV Antigen Specific T Cells as a Component of a Cure Strategy", JPT Peptide Technologies, Nov. 1, 2015.
Morse et al ( Expert Opin. Biol. Ther, 2002, 2, pp. 237-247.
Plautz et al., ( Archivum Immunologiae et Therapiae Experimentalis, 2003, 51, 245-257.
Ramos et al., "CAR-T Cell therapy for Lymphoma," HHS Public Access Author Manuscript, Epub Jan. 4, 2016, pp. 1-23.
Ramos et al., "Chimeric T Cells for Therapy of CD30+ Hodgkin and Non-Hodgkin Lymphomas," American Society of Hematology, Epub Dec. 3, 2015, pp. 1-3.
Ramos et al., "Clinical and immunological responses after CD30-specific chimeric antigen receptor-redirected lymphocytes," The Journal of Clinical Investigation, vol. 127, No. 9, Epub Sep. 2017, pp. 3462-3471.

(Continued)

*Primary Examiner* — Michail A Belyavskyi

(74) *Attorney, Agent, or Firm* — Norton Rose Fulbright US LLP

(57) ABSTRACT

Embodiments of the disclosure concern methods and compositions for immunotherapy for diseases and malignancies associated with viruses other than HPV or with non-virus-associated diseases and malignancies, such as wherein the VST encodes a CAR specific for a non-viral cancer and the VST can be stimulated in vitro or in vivo using viruses, viral vaccines or oncolytic viruses. In specific embodiments, methods concern production of immune cells that target one or more antigens of HIV, EBV, CMV, adenovirus, vaccinia virus, and/or VZV, including methods with stimulation steps that employ IL-7 and IL-15, but not IL-2, IL-4, or both. Other specific embodiments utilize stimulations in the presence of certain cells, such as costimulatory cells and certain antigen presenting cells.

11 Claims, 31 Drawing Sheets

(56) References Cited

OTHER PUBLICATIONS

Salvado et al., "Chimeric antigen receptors (CARs) from Bench-to-Bedside," National Institutes of Health, NIH Public Access Author Manuscript, Epub 2013, pp. 1-7.
Savoldo, et al; Epstein Barr Virus-Specific Cytotoxic T Lymphocytes Expressing the Anti-CD30z Artificial Chimeric T-Cell Receptor for immunotherapy for Hodgkin Disease; The American Society of Hematology; Blood, Oct. 1, 2007; vol. 110, No. 7.
Teschner D. et al., "Depletion of naive T cells using clinical grade magnetic CD45RA beads: a new approach for GVHD prophylaxis", Bone Marrow Transplantation , Aug. 12, 2013, vol. 49, No. 1, pp. 138-144.
Piersma et al. "Human papilloma virus specific T cells infiltrating cervical cancer and draining lymph nodes show remarkably frequent use of HLA-DQ and-DP as a restriction element", International Journal of Cancer, Feb. 1, 2008, 122(1):486-494.

* cited by examiner

Day 0: Optional: Deplete CD45RA+ T-cells from PBMC
Pulse PBMCs or CD45RA-depleted PBMCs with viral peptides
Optional: Use irradiated HLA-ve LCL in first stimulation
Day 9: 2nd stimulation with peptide-pulsed irradiated autologous ATCs and HLA-ve LCLs
Day 16: Cryopreserve Note: CD45RA+ cells fail to expand beyond second stimulation

* Whole PBMCs with DCs but the depleted conditions were generated without using DCs

No significant difference (p=0.25) in proliferation between DC and PBMC initiated VSTs

PLATFORM FOR ACTIVATION AND EXPANSION OF VIRUS-SPECIFIC T-CELLS

This application claims priority to U.S. application Ser. No. 16/331,494, now abandoned, which was a national phase entry of PCT Serial No. PCT/US2017/051284, filed Sep. 13, 2017, that claimed priority to U.S. Provisional Patent Application Ser. No. 62/395,438, filed Sep. 16, 2016, all of which are incorporated by reference herein in their entirety.

STATEMENT REGARDING FEDERALLY SPONSORED RESEARCH OR DEVELOPMENT

This invention was made with government support under CA126752 and CA094237 awarded by the National Institutes of Health. The government has certain rights in the invention.

TECHNICAL FIELD

The present disclosure concerns at least the fields of immunology, cell biology, molecular biology, and medicine, including cancer medicine.

BACKGROUND

Antigen-specific T-cell activation and expansion requires 3 signals. Signal 1 requires the T-cell receptor (TCR) to bind its cognate peptide-MHC complex. Signal 2 requires stimulation of costimulatory receptors on the T-cell surface, and signal 3 is derived from cytokines. The signals are required about once every 7 to 14 days to maintain the expansion of antigen-specific T-cells in vitro. In the absence of any one of these signals, T-cells will fail to proliferate and may become anergic or die. These requirements introduce several challenges, especially when activating tumor antigen-specific T-cells from cancer patients, whose tumor antigen-specific T-cells are usually anergic (unresponsive to activation) or otherwise dysfunctional.

Major challenges for antigen-specific T-cell activation and expansion that have been addressed include:

1. Tumor-induced T-cell anergy. Circulating T-cells have been anergized by tumors and are difficult to expand from the blood of cancer patients; and 2. Expansion of exclusively antigen-specific CD4+ and CD8+ T-cells requires repeated stimulation of antigen-specific T-cells with autologous antigen-presenting cells expressing tumor antigens on both HLA class I and class II molecules, and costimulatory molecules. If stimulation is too potent, non-specific bystander cells are expanded diluting the antigen-specific T-cells.

Autologous dendritic cells (DCs) are potent antigen-presenting cells, but their numbers are limiting; they do not divide and their monocyte precursors less than 10% of blood mononuclear cells (PBMCs). Large amounts of blood would be required to obtain sufficient DCs for T-cell expansion (300 mLs to 1 liter of blood).

Autologous EBV-transformed B-lymphoblastoid cells lines (LCLs) are also excellent antigen-presenting cells, but it takes at least 6 weeks to establish LCLs from patients and LCLs express highly immunogenic EBV antigens that compete with weaker EBV and non-EBV antigens.

The present disclosure addresses a variety of issues associated with antigen-specific T-cell activation and expansion and provides relief for a long-felt need in the art to treat virus-associated diseases and malignancies with effective immunotherapies.

BRIEF SUMMARY

The present disclosure is directed to methods and compositions that concern immune system cells that immunogenically recognize particular targets. In some embodiments, the present invention concerns the development of virus-specific T cells (VSTs) (that may also be referred to as virus antigen-specific T cells or antigen-specific T cell) that target a biological moiety that elicits an immune response in an individual. In specific embodiments, the present disclosure concerns the development of VSTs that target a viral antigen, including a viral disease-associated antigen. Embodiments of the disclosure include production of cells that are CD8+ T cells, CD4+ T cells, and cells that do no kill but produce one or more cytokines. In some cases, a mixture of cytotoxic T-cells is produced, and the mixture targets more than one viral antigen, including more than one antigen of more than one virus, in some cases. In particular embodiments, the virus is not human papilloma virus (HPV). Embodiments of the disclosure concern the generation and/or expansion of non-HPV-specific T-cells.

Embodiments of the disclosure concern methods and compositions for providing therapy to individuals infected with a non-HPV virus or that have virus-associated diseases and malignancies that are not associated with HPV, including cancers associated with certain viruses. In specific embodiments, the disclosure regards methods and compositions for adoptive cellular immunotherapy that can target virus-associated medical conditions and are therapeutic therefor.

In certain aspects, the present disclosure concerns the development of a plurality of T-cells that target antigens from EBV, CMV, adenovirus, vaccinia virus, HIV, and/or VZV, for example. The present disclosure provides significant and non-obvious improvements on methods for generating T cell lines with specificity against antigens from EBV, CMV, adenovirus, vaccinia virus, and/or VZV, for example, wherein the virus is not HPV.

In some embodiments of the disclosure, an individual is in need of the methods and/or compositions of the invention. In certain embodiments, an individual has been exposed to EBV, CMV, adenovirus, vaccinia, and/or VZV, for example (the presence of which may or may not be known for the individual), or the individual is suspected of having been exposed to or at risk for being exposed to EBV, CMV, adenovirus, vaccinia virus, and/or VZV, for example. In certain embodiments, the individual has or is suspected of having or is at risk for having disease associated with EBV, CMV, adenovirus, vaccinia, and/or VZV, or has been vaccinated with EBV, CMV, adenovirus, VZV or vaccinia virus, for example.

In specific embodiments of at least part of the method, certain antigen(s) associated with EBV, CMV, adenovirus, vaccinia, and/or VZV are presented to APCs in the form of one or more peptides that span some or all of certain antigen(s). The antigenic peptides may be provided to the APCs in a library of peptide mixtures, which may be referred to as pepmixes. In certain aspects of the disclosure, there is pooling of a variety of pepmixes for exposure to the APCs. APCs that present the antigens on MHC molecules may be exposed to peripheral blood T-cells under certain conditions to result in stimulation of T-cells specific for the certain viral antigen(s).

In some embodiments, there are methods for stimulating peripheral blood cells, such as peripheral blood T-cells, wherein the method comprises stimulating peripheral blood T-cells with antigen presenting cells in the presence of interleukin (IL)-7 and IL-15 and, in at least some cases, in the absence of one or more other cytokines, such as IL-6 and/or IL-12, wherein the antigen presenting cells were previously exposed to one or more peptides, wherein the peptides comprise sequence that corresponds to at least part of the sequence of one or more proteins of a virus that is not HPV.

Methods for stimulating T-cells specific for a non-HPV virus or for an antigen from a non-HPV virus include stimulating T-cells specific for the virus or for the antigen with antigen presenting cells in the presence of IL-7 and IL-15, and optionally in the presence of co-stimulatory cells, wherein the antigen presenting cells were previously exposed to one or more peptides, wherein the peptides comprise sequence that corresponds to at least part of the sequence of one or more proteins of the virus.

In some cases there are methods of producing therapeutic T-cells for non-HPV virus-associated disease(s), comprising the step of stimulating peripheral blood T-cells with antigen presenting cells in the presence of one or more of interleukin IL-7 and IL-15 and, in at least some cases, optionally in the absence of one or more other cytokines, such as IL-6 and/or IL-12, wherein the antigen presenting cells were previously exposed to one or more peptides, wherein the peptides comprise sequence that corresponds to at least part of the sequence of one or more proteins of a virus that is not HPV, wherein the stimulating produces T-cells therapeutic for virus-associated diseases and malignancies that are not HPV-associated diseases.

In specific embodiments, there are methods of producing therapeutic T-cells for virus-associated diseases and malignancies other than HPV-associated diseases, comprising the step of stimulating T-cells specific for the virus or for a viral antigen with antigen presenting cells in the presence of one or more of interleukin IL-7 and IL-15, and optionally in the presence of co-stimulatory cells, wherein the antigen presenting cells were previously exposed to one or more peptides, wherein the peptides comprise sequences that corresponds to at least part of the sequence of one or more proteins of a virus that is not HPV, wherein the stimulating produces T-cells therapeutic for one or more virus-associated diseases and malignancies.

In some cases, the peripheral blood T-cells being stimulated are obtained from a prior stimulation of peripheral blood cells, such as stimulating peripheral blood cells with antigen presenting cells in the presence of IL-7 and IL-15, and in at least some cases in the presence of one or more other cytokines, such as IL-6 and/or IL-12, wherein the antigen presenting cells were previously exposed to one or more peptides, wherein the peptides comprise sequence that corresponds to at least part of the sequence of one or more proteins of a virus that is not HPV. As such, prior to stimulating the peripheral blood T-cells, the methods may further comprise stimulating peripheral blood cells with antigen presenting cells in the presence of IL-7 and IL-15, and in at least some cases in the presence of IL-6 and/or IL-12, wherein the antigen presenting cells were previously exposed to one or more peptides, wherein the peptides comprise sequence that corresponds to at least part of the sequence of one or more proteins of a virus that is not HPV, to produce peripheral blood T-cells.

In some embodiments the one or more peptides comprise sequence that corresponds to at least part of the sequence of one or more proteins of a virus that is not HPV. In some embodiments the one or more peptides may be a library of peptides, which may also be referred to as a collection of peptides. In specific embodiments the method may produce T-cells specific for EBV, CMV, adenovirus, vaccinia, and/or VZV or for an antigen from EBV, CMV, adenovirus, Vaccinia, and/or VZV. In some embodiments the method may expand a population of T-cells present in the peripheral blood T-cells that are specific for EBV, CMV, adenovirus, vaccinia, and/or VZV or for an antigen from EBV, CMV, adenovirus, vaccinia, and/or VZV.

APCs used in one or more methods of the disclosure include monocytes, dendritic cells (DC), B-Blasts (BB), and/or PBMCs, for example. In particular embodiments the antigen presenting cells are activated T-cells.

In some embodiments the stimulation of T-cells specific for a virus other than HPV or for an antigen other than one from HPV is not a first stimulation step. The T-cells being stimulated cells may be the product of a prior stimulation. In certain embodiments stimulation of T-cells specific for a virus other than HPV or for an antigen other than HPV comprises stimulating T-cells specific for the virus or for the viral antigen with antigen presenting cells in the presence of interleukin (IL)-7, IL-15, and in the presence of one or more types of co-stimulatory cells.

In some embodiments the method may produce T-cells specific for a non-HPV virus or for an antigen that is not an HPV antigen. In some embodiments the method may expand a population of T-cells specific for a virus or for an antigen other than HPV.

In specific embodiments, stimulation of peripheral blood T-cells in the presence of IL-7 and IL-15 optionally occurs in the absence of IL-2. In some embodiments stimulation of peripheral blood T-cells in the presence of IL-7 and IL-15 optionally occurs in the absence of at least IL-4; although in some cases IL-4 is added, for example to increase CD4+ T cells. In some embodiments stimulation of peripheral blood T-cells in the presence of IL-7 and IL-15 occurs optionally in the absence of IL-6. In some embodiments stimulation of peripheral blood T-cells in the presence of IL-7 and IL-15 but alternatively may occur in the absence of IL-7 and/or IL-15. In some embodiments stimulation of peripheral blood T-cells in the presence of IL-7 and IL-15 optionally occurs in the absence of IL-12. In some embodiments stimulation of peripheral blood T-cells in the presence of IL-7 and IL-15 optionally occurs in the absence of IL-21.

In some embodiments, the peripheral blood T-cells utilized in methods of the disclosure may be present in a population of peripheral blood mononuclear cells (PBMCs) or are obtained or isolated therefrom. The PBMCs in the population may be non-adherent PBMCs, or may be CD45RA-depleted PBMCs (for example, to eliminate a combination of Tregs, NK cells and naïve T-cells). The antigen presenting cells may be dendritic cells, B-blasts, or PBMCs, for example.

Methods of the present disclosure include methods of producing therapeutic T-cells for virus-associated diseases and malignanices that are not HPV. The stimulation of cells may produce T-cells that are therapeutic for virus-associated diseases and malignancies that are not HPV-associated diseases. In some embodiments a method of producing therapeutic T-cells for HPV-associated diseases is provided, the method comprising:

(i) stimulating peripheral blood cells, wherein the method comprises stimulating peripheral blood T-cells with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of a non-HPV virus; or (ii) stimulating T-cells obtained from (i) with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of the virus, wherein (ii) is optionally repeated one or more times;

(iii) stimulating T-cells obtained from (ii) with antigen presenting cells in the presence of IL-7 and IL-15, and optionally in the presence of co-stimulatory cells, wherein the antigen presenting cells were previously exposed to one or more peptides, wherein the peptides comprise sequence that corresponds to at least part of the sequence of one or more proteins of the virus, wherein (iii) is optionally repeated one or more times.

In some embodiments the antigen presenting cells used in (i) and (ii) are monocytes, dendritic cells (DC) B-Blasts (BB) or PBMCs. In some embodiments the antigen presenting cells used in (iii) are activated T-cells, dendritic cells (DC), B-Blasts (BB) or PBMCs. In some embodiments the antigen presenting cells used in (iii) are different than the antigen presenting cells used in (i) and/or (ii). In preferred embodiments the antigen presenting cells used in (iii) are activated T-cells.

In particular embodiments, stimulation occurs in the presence of co-stimulatory cells. In some embodiments the co-stimulatory cells are one or more cell types selected from the group consisting of CD80+ cells, CD86+ cells, CD83+ cells, 4-1BBL+ cells, and a combination thereof. The co-stimulatory cells may be CD80+/CD86+/CD83+/4-1BBL+ cells. The co-stimulatory cells may be HLA-negative lymphoblastoid cells.

In some particular embodiments, methods of the present disclosure are for producing T-cells specific for EBV, CMV, adenovirus, Vaccinia, and/or VZV. In some particular embodiments methods of the present disclosure are for producing T-cells specific for diseases and malignanices associated with EBV, CMV, adenovirus, Vaccinia, and/or VZV.

In some embodiments, peripheral blood T-cells may be obtained from an individual that is known to be infected or suspected of being infected or vaccinated with EBV, CMV, adenovirus, vaccinia, and/or VZV. Antigen presenting cells may be obtained from an individual that is known to be infected or suspected of being infected or vaccinated with EBV, CMV, adenovirus, vaccinia virus, and/or VZV.

In some embodiments, the method may occur in the absence of exposing the T-cells produced by the method to activated B cells that were previously exposed to a library of peptides.

In some embodiments, antigen presenting cells may be autologous or allogeneic to an individual intended to be treated with the therapeutic T-cells obtained.

In some embodiments, the one or more peptides comprise sequence that corresponds at least part to the sequence of one or more proteins of EBV, CMV, adenovirus, vaccinia virus, and/or VZV. The peptides may correspond to a contiguous amino acid sequence present within the viral protein. A peptide may have a length of at least or no more than 8, 9, 10, 11, 12, 13, 14, 15, 16, 17, 18, 19, or 20 amino acids in length, or of 15 amino acids in length. The collection of peptides may form a library and peptides in the library may overlap in sequence with other peptides by any suitable amount, including 3, 4, 5, 6, 7, 8, 9, 10, 11, 12, 13, or 14 amino acids, for example. The peptides may comprise sequence that corresponds to the viral protein.

T-cells produced by the methods of the present disclosure may be isolated and/or purified, e.g., isolated/purified from other cells.

In some embodiments, a therapeutically effective amount of T-cells produced by the methods of the present disclosure are provided to an individual that has been exposed to a virus that is not HPV, or that has a virus-associated disease that is not from HPV. In a related aspect T-cells produced by the methods of the present disclosure are provided for use in the treatment of virus-associated disease that is not from HPV. In another related aspect the use of T-cells produced by the method of the present disclosure are provided for use in the manufacture of a medicament for use in the treatment of virus-associated disease that is not HPV.

In particular embodiments, the methods of the disclosure encompass the use of viruses to promote the expansion of VSTs modified with one or more engineered receptors, for example chimeric antigen receptors (CARs). For example, if the virus was VZV and the VSTs were VZV-specific (VZVSTs), then a VZV vaccine (e.g., ZOSTAVAX or VARIVAX) could be used to stimulate proliferation of CAR-modified VZVSTs after infusion. If the VSTs were specific for an oncolytic virus such as adenovirus, maraba virus or vaccinia or VSV, then the oncolytic virus (OV) could not only kill tumor cells, but also stimulate CAR-modified T-cells specific for that oncolytic virus. The CAR-modified OV-specific T cells (CAR-OVSTs) could then kill uninfected or metastatic tumors cells via the CAR.

The individual to be treated may be a human. The individual may be a patient. The individual may have been exposed to EBV, CMV, adenovirus, vaccinia virus, and/or VZV, or has a disease associated with EBV, CMV, adenovirus, vaccinia virus, and/or VZV. The disease may be a neoplasm, such as a cancer of any kind.

The individual may have received, be receiving, or will receive an additional therapy for the disease including, where appropriate, an additional cancer therapy, such as surgery, radiation, hormone therapy, chemotherapy, immunotherapy, or a combination thereof.

The individual may be determined as having virus-associated cancer that is not from HPV.

Methods according to the present disclosure that involve steps of cell stimulation may be performed in vitro or ex vivo. The term "in vitro" is intended to encompass studies with materials, biological substances, cells and/or tissues in laboratory conditions or in culture. "Ex vivo" refers to something present or taking place outside an organism, e.g. outside the human or animal body, which may be on tissue (e.g. whole organs) or cells taken from the organism.

In one embodiment, there is a method for stimulating peripheral blood cells, the method comprising stimulating peripheral blood T-cells with antigen presenting cells in the presence of interleukin (IL)-7 and IL-15, wherein the antigen presenting cells were previously exposed to one or more peptides, wherein the peptides comprise sequence that corresponds to at least part of the sequence of one or more proteins of one or more viruses that are not HPV.

In a particular embodiment, there is a method of producing viral antigen-specific T-cells, comprising the step of stimulating a population of peripheral blood T-cells with antigen presenting cells in the presence of IL-7 and IL-15 (for example, ≥100 ng/mL), wherein the antigen presenting cells are or were previously exposed to a library of peptides, wherein the peptides comprise sequence that corresponds to at least part of the sequence of one or more proteins of one or more viruses that are not HPV.

In particular embodiments of the method, a population of peripheral blood T-cells have reduced levels, compared to normal levels, of one or more of the following: 1) NK cells; 2) naïve cells that can grow as bystander cells; and/or 3) T-regulatory cells, for example when CD45RA+ cells have been depleted from a starting PBMC or apheresis product. In certain cases, PBMCs or peripheral blood T-cells obtained therefrom are subject to a step of reducing the levels of one or more of the following: 1) NK cells; 2) naïve cells that can grow as bystander cells; and/or 3) T-regulatory cells. Peripheral blood T-cells may be present in a population of peripheral blood mononuclear cells (PBMCs) or are obtained or isolated therefrom. PBMCs or an apheresis product may be depleted of one or more of the following: 1) NK cells; 2) naïve cells that can grow as bystander cells; and/or 3) T-regulatory cells. The PBMCs may be CD45RA-depleted PBMCs. PBMCs in the population may be non-adherent PBMCs. In specific embodiments, the PBMCs may be depleted of myeloid cells that are suppressive myeloid cells, for example by adherence or by other depletion methods.

Viruses encompassed by the disclosure include those from the family Herpesviridae or is a poxvirus, adenovirus, polyomavirus, lentivirus, rhabdovirus or other oncolytic virus. In specific embodiments, the virus is selected from the group consisting of Epstein-Barr virus (EBV), Cytomegalovirus (CMV), adenovirus, vaccinia virus, and/or Varicella zoster virus (VZV), HIV, influenza, marabavirus vesicular stomatitis virus or any other oncolytic virus.

Antigen presenting cells utilized in methods of the disclosure may be dendritic cells or PBMCs, in specific embodiments.

In methods encompassed by the disclosure a stimulating step occurs in the absence of IL-6, IL-12, IL-2, IL-4, IL-21, or a combination thereof. In certain embodiments, a stimulating step occurs in the presence of costimulatory cells, such as costimulatory cells that are CD80+, CD86+, CD83+, 4-1BBL+, or a combination thereof, or wherein the costimulatory cells are HLV-negative lymphoblastoid cells. The stimulating may occur in the presence of activated T-cells, dendritic cells, PBMCs, or HLA-negative costimulatory cells. The stimulating may occur in the presence of activated T-cells, dendritic cells, PBMCs, or HLA-negative costimulatory cells, the stimulating step is not a first stimulation step. Activated T-cells may be autologous to the individual. Stimulating may occur in the presence of pepmixes, pepmix-pulsed autologous activated T-cells, in the presence of HLA-negative costimulatory cells, or both. In specific cases, when the stimulating occurs in the presence of pepmix-pulsed autologous activated T-cells, in the presence of HLA-negative costimulatory cells, or both, the stimulating step is not a first stimulation step. In such cases, two stimulations are performed and the second stimulation occurs in the presence of costimulatory cells and pepmix-pulsed (autologous activated T cells (AATCs).

Peptide libraries utilized in methods of the disclosure may comprise peptides of at least or no more than 8, 9, 10, 11, 12, 13, 14, 15, 16, 17, 18, 19, 20, 21, 22, 23, 24, 25, 26, 27, 28, 29, 30, or more amino acids in length. In specific cases, the peptide library comprises peptides of 15 amino acids in length and/or peptides in the library overlap in sequence with other peptides by 11 amino acids.

In certain embodiments, T-cells produced by a first stimulating step are subject to one or more subsequent stimulating steps, such as a subsequent stimulating step that occurs in the presence of IL-7 and IL-15. A subsequent stimulating step may occur in the presence of activated T-cells, costimulatory cells, IL-7, and/or IL-15. In specific cases, the method occurs in the absence of exposing the T-cells produced by the method to activated B cells that were previously exposed to a library of peptides.

In some cases, cells produced by the method are modified to express a gene product from an expression vector, such as modified to express a chimeric antigen receptor, αβ T-cell receptor, or combination thereof.

In certain cases, a therapeutically effective amount of T-cells produced by the method are provided to an individual that has been exposed to EBV, CMV, adenovirus, vaccinia virus, HIV, and/or VZV, that is seropositive for EBV, CMV, adenovirus, vaccinia virus, HIV, and/or VZV, or that has disease associated with EBV, CMV, adenovirus, vaccinia virus, HIV, and/or VZV. In specific aspects, the individual is determined as having a medical condition associated with EBV, CMV, adenovirus, vaccinia virus, HIV, and/or VZV. In certain embodiments, the cancer is a non-viral cancer.

In specific cases, one or more steps of the method lack the presence of exogenously added IL-4, IL-2, or both.

In an embodiment, there is a method for stimulating T-cells specific for a virus other than HPV, comprising stimulating T-cells specific for the virus with antigen presenting cells in the presence of IL-7 and IL-15 and in the presence of co-stimulatory cells, wherein the antigen presenting cells were previously exposed to one or more peptides, wherein the peptides comprise sequence that corresponds to at least part of the sequence of one or more proteins of a virus other than HPV.

In another embodiment, there is a method of producing therapeutic T-cells for a virus-associated disease or a non-virus-associated disease, the method comprising the step of stimulating T-cells specific for a virus other than HPV with antigen presenting cells in the presence of one or more of IL-7 and IL-15 and in the presence of co-stimulatory cells, wherein the antigen presenting cells were previously exposed to one or more peptides, wherein the peptides comprise sequence that corresponds to at least part of the sequence of one or more proteins of a virus other than HPV, wherein the stimulating produces T-cells therapeutic for the virus-associated disease or malignancy.

The disclosure encompasses at least the following:

1. A method for stimulating peripheral blood cells, the method comprising stimulating peripheral blood T-cells with antigen presenting cells in the presence of interleukin (IL)-7 and IL-15, wherein the antigen presenting cells were previously exposed to one or more peptides, wherein the peptides comprise sequence that corresponds to at least part of the sequence of one or more proteins of one or more viruses that are not human papillomavirus (HPV).

2. A method of producing viral antigen-specific T-cells, comprising the step of stimulating a population of peripheral blood T-cells with antigen presenting cells in the presence of IL-7 and IL-15, wherein the antigen presenting cells are or were previously exposed to a library of peptides, wherein the peptides comprise sequence that corresponds to at least part of the sequence of one or more proteins of one or more viruses that are not HPV.

3. The method of paragraph 1 or 2, wherein the concentration of IL-15 is ≥100 ng per mL.

4. The method of paragraph 1, 2, or 3, wherein the stimulating occurs in the absence of IL-6, IL-12, IL-2, IL-4, IL-7, IL-21, or a combination thereof.

5. The method of any one of paragraphs 1-4, wherein the population of peripheral blood T-cells have reduced levels, compared to normal levels, of one or more of the following: 1) NK cells; 2) naïve cells that can grow as bystander cells; and/or 3) T-regulatory cells.

6. The method of paragraph 5, wherein the PBMCs or peripheral blood T-cells obtained therefrom are subject to a step of reducing the levels of one or more of the following: 1) NK cells; 2) naïve cells that can grow as bystander cells; and/or 3) T-regulatory cells.

7. The method of any one of paragraphs 1-6, wherein the virus is from the family Herpesviridae or is a poxvirus, adenovirus, polyomavirus, lentivirus, rhabdovirus or other oncolytic virus.

8. The method of any one of paragraphs 1-7, wherein the virus is selected from the group consisting of Epstein-Barr virus (EBV), Cytomegalovirus (CMV), adenovirus, Vaccinia, and/or Varicella zoster virus (VZV), HIV, influenza, marabavirus vesicular stomatitis virus and an oncolytic virus.

9. The method of any one of paragraphs 1-8, wherein the peripheral blood T-cells are present in a population of peripheral blood mononuclear cells (PBMCs) or are obtained or isolated therefrom.

10. The method of paragraph 6 or 9, wherein the PBMCs or apheresis product are depleted of one or more of the following: 1) NK cells; 2) naïve cells that can grow as bystander cells; and/or 3) T-regulatory cells.

11. The method of paragraph 10, wherein the PBMCs are CD45RA-depleted PBMCs and/or are CD45RO-depleted PBMCs.

12. The method of any one of paragraphs 6 or 9-11, wherein the PBMCs in the population are non-adherent PBMCs 13. The method of any one of paragraphs 1-12, wherein the antigen presenting cells are dendritic cells or PBMCs.

14. The method of any one of paragraphs 1-12, wherein a stimulating step occurs in the presence of costimulatory cells.

15. The method of paragraph 14, wherein the costimulatory cells are CD80+, CD86+, CD83+, 4-1BBL+, or a combination thereof, or wherein the costimulatory cells are HLV-negative lymphoblastoid cells.

16. The method of any one of paragraphs 1-15, wherein the stimulating occurs in the presence of activated T-cells, dendritic cells, PBMCs, or HLA-negative costimulatory cells.

17. The method of paragraph 16, wherein when the stimulating occurs in the presence of activated T-cells, dendritic cells, PBMCs, or HLA-negative costimulatory cells, the stimulating step is not a first stimulation step.

18. The method of paragraph 16 or 17, wherein the activated T-cells are autologous to the individual.

19. The method of any one of paragraphs 1-18, wherein the stimulating occurs in the presence of pepmixes, pepmix-pulsed autologous activated T-cells, in the presence of HLA-negative costimulatory cells, or both.

20. The method of paragraph 19, wherein when the stimulating occurs in the presence of pepmix-pulsed autologous activated T-cells, in the presence of HLA-negative costimulatory cells, or both, the stimulating step is not a first stimulation step.

21. The method of any one of paragraphs 1-20, wherein the peptide library comprises peptides of at least or no more than 8, 9, 10, 11, 12, 13, 14, 15, 16, 17, 18, 19, 20, 21, 22, 23, 24, 25, 26, 27, 28, 29, 30, or more amino acids in length.

22. The method of any one of paragraphs 1-21, wherein the peptide library comprises peptides of 15 amino acids in length.

23. The method of any one of paragraphs 1-22, wherein peptides in the library overlap in sequence with other peptides by 11 amino acids.

24. The method of any one of paragraphs 1-23, wherein T-cells produced by a first stimulating step are subject to one or more subsequent stimulating steps.

25. The method of paragraph 24, wherein a subsequent stimulating step occurs in the presence of IL-7 and IL-15.

26. The method of paragraph 24 or 25, wherein a subsequent stimulating step occurs in the presence of activated T-cells, costimulatory cells, IL-7, and IL-15.

27. The method of any one of paragraphs 1-26, wherein the method occurs in the absence of exposing the T-cells produced by the method to activated B cells that were previously exposed to a library of peptides.

28. The method of any one of paragraphs 1-27, wherein the cells are modified to express a gene product from an expression vector.

29. The method of paragraph 29, wherein the cells are modified to express a chimeric antigen receptor, γδT-cell receptor, or combination thereof.

30. The method of any one of paragraphs 1-29, wherein a therapeutically effective amount of T-cells produced by the method are provided to an individual that has been exposed to EBV, CMV, adenovirus, Vaccinia, HIV, and/or VZV, that is seropositive for EBV, CMV, adenovirus, Vaccinia, HIV, and/or VZV, or that has disease associated with EBV, CMV, adenovirus, Vaccinia, HIV, and/or VZV.

31. The method of any one of paragraphs 1-30, wherein the individual is determined as having a medical condition associated with EBV, CMV, adenovirus, Vaccinia, HIV, and/or VZV.

32. The method of any one of paragraphs 1-31, wherein one or more steps of the method lack the presence of exogenously added IL-4, IL-2, or both.

33. A method for stimulating T-cells specific for a virus other than HPV, comprising stimulating T-cells specific for the virus with antigen presenting cells in the presence of IL-7 and IL-15 and in the presence of co-stimulatory cells, wherein the antigen presenting cells were previously exposed to one or more peptides, wherein the peptides comprise sequence that corresponds to at least part of the sequence of one or more proteins of a virus other than HPV.

34. A method of producing therapeutic T-cells for a virus-associated disease or a non-virus-associated disease, the method comprising the step of stimulating T-cells specific for a virus other than HPV with antigen presenting cells in the presence of one or more of IL-7 and IL-15 and in the presence of co-stimulatory cells, wherein the antigen presenting cells were previously exposed to one or more peptides, wherein the peptides comprise sequence that corresponds to at least part of the sequence of one or more proteins of a virus other than HPV, wherein the stimulating produces T-cells therapeutic for the viral-associated disease.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION

The scope of the present application is not intended to be limited to the particular embodiments of the process, machine, manufacture, composition of matter, means, methods and steps described in the specification.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The present disclosure concerns the production and use of therapeutic T-cells for individuals that are in need of EBV-, CMV-, adenovirus-, vaccinia virus-, and/or VZV-specific T-cells, including for treating medical conditions associated with one or more of these viruses in an individual. In some embodiments, the disclosure concerns the production and use of therapeutic T-cells for a non-viral cancer; in such cases, one or more CARs are expressed in the VSTs and vaccination or oncolytic viruses are used to stimulate the CAR-VSTs via their T-cell receptors. In particular embodiments, therapeutic T-cells are generated upon stimulation of APCs in the presence of IL-7 and IL-15, wherein the APCs were previously exposed to a peptide library directed to one or more viral antigens.

Figure 2:
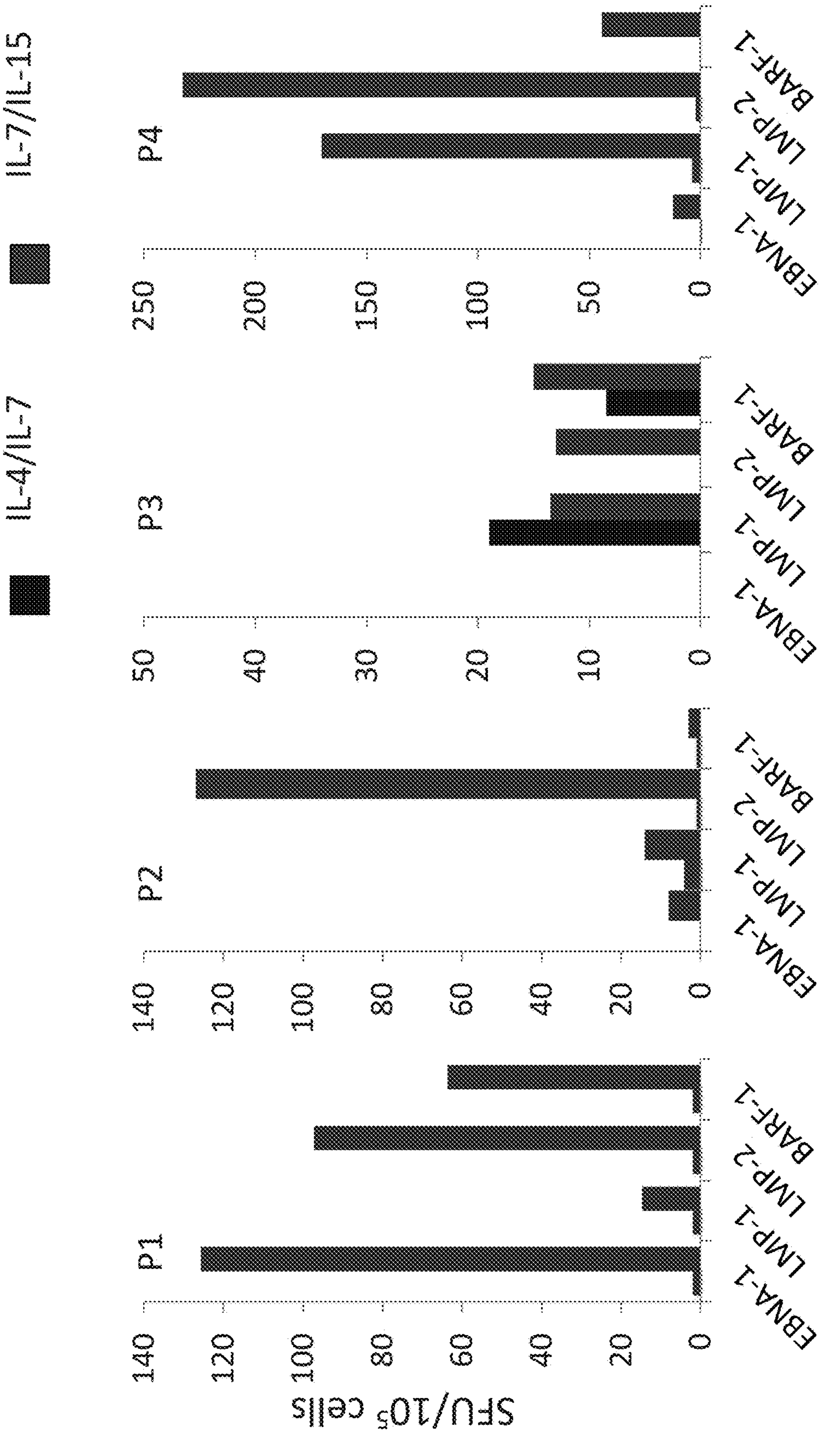
FIG. 2 demonstrates improved specificity of methods of the disclosure that employ IL-7 and IL-15 as compared to known methods that employ IL-4 and IL-7.

In particular aspects, the present disclosure addresses challenges related to adoptive T cell transfer. For example, to address tumor induced T-cell anergy, the inventors have evaluated various combinations of cytokines and determined that at least in some cases a high dose of IL-15 combined with IL-7 facilitates the expansion of anergic antigen-specific T-cells (FIG. 2). Thus for the first stimulation antigen-specific T-cells are activated by pulsing PBMCs with overlapping peptide libraries (pepmixes that comprise 15mer amino acids overlapping by 11 amino acids and spanning the proteins of interest, for example) in the presence of IL7 (10 ng per mL) and IL15 (100 ng per mL). Herein the inventors have evaluated antigens from several different viruses to make virus-specific T-cells (VSTs).

To address one problem of the antigen-presenting cell, the inventors have evaluated an antigen-presenting cell complex in which autologous activated T-cells pulsed with peptides provide signal 1 (binding of T-cell receptor (TCR) to its cognate peptide-MHC complex), and an HLA-negative LCL, provides co-stimulation (signal 2). An alternative artificial costimulatory cell line is the HLA-negative K562 cell line genetically modified to express CD80, CD86, CD83 and 4-1BB ligand, for example. In this case co-stimulation is provided in trans, on a different cell type. In such cases, HLA antigens must be absent because these molecules are potent antigens and can activate allospecific T-cells, and EV-LCLs naturally express a range of costimulatory molecules.

This strategy is able to induce log-fold expansion of VSTs with specificity for the stimulating antigens. Because in some donors this strategy potently expands NKcells, the inventors have also introduced a depletion step. For example, PBMCs may be depleted of CD45RA+ T-cells. This depletes not only NK cells but also naïve T-cells and natural T regulatory cells. VSTs grown from CD45RA-depleted PBMCs have higher antigen-specificity, show greater fold expansion and have minimal NK cells. Further from some individuals the inventors were able to grow VSTs only if they first depleted RA+ T-cells from PBMCs.

I. Viral Antigen(s) and Generation of Pepmixes

Methods of the disclosure utilize antigen-presenting cells that present mixtures of peptides to T-cells. Such "loaded" APCs are generated prior to exposure to peripheral blood T-cells for stimulation, and the generation of the loaded APCs may or may not be performed by the individual or entity that performs the stimulation step for the peripheral blood T-cells. Thus, in some embodiments, an effective amount of a library of peptides is provided to APCs as part of methods that ultimately generate therapeutic virus-specific T cells (VSTs) or antigen-specific T-cells. In methods of the disclosure, prior to a stimulation step, APCs are exposed to a sufficient amount of the library of peptides. The library, in particular cases, comprises a mixture of peptides ("pepmixes") that span part or all of the same antigen. In particular embodiments, peptides for the APCs are non-natural.

In utilizing a library of mixtures of peptides from one or more antigens, the various peptides may come from any part of a given protein, but in specific cases the peptides span the length of the majority or all of the protein, wherein the sequence of the peptides overlap at least in part to facilitate coverage of the entire desired region of the specific antigen (s). In some cases the peptides span the length or one or more known epitopes or domains of the respective antigen to which the peptides correspond. Certain regions may be covered by peptides that span the length of the region, including a region such as a N-terminal domain, C-terminal domain, extracellular domain, or intracellular domain, for example.

The antigens from which the peptides are derived are antigens for EBV, CMV, adenovirus, vaccinia virus, and/or VZV that may be of any kind, but in specific embodiments the antigens are such that they allow for targeting for cytotoxic T-cells to medical conditions associated with EBV, CMV, adenovirus, vaccinia virus, and/or VZV infection, respectively. In particular embodiments, the peptides are derived from, or have sequence that corresponds to, at least part of one or more antigens of at least one type of EBV, CMV, adenovirus, vaccinia virus, or VZV. In some cases, a pepmix library includes peptides corresponding to one or more antigens from a single virus, and those peptides may or may not provide sequence coverage across the entire antigen(s) in question. In other cases, a pepmix library includes peptides corresponding to one or more antigens from more than one virus, and those peptides may or may not provide sequence coverage across the entire antigen(s) in question. The pepmix may or may not be enriched for peptides corresponding to one or more certain regions of one or more certain antigens or corresponding to the entirety of one or more certain antigens.

Pepmixes utilized in the disclosure may be from commercially available peptide libraries and/or may be synthetically generated. Examples of available libraries include those from JPT Technologies (Springfield, VA) or Miltenyi Biotec (Auburn, CA). The skilled artisan based on known sequences of viral antigens, for example, would have sufficient information to be able to generate peptides that correspond to their exemplary, respective sequences. The skilled artisan, based on known sequences of antigens from these well-known viruses, for example, would have sufficient information to be able to generate peptides that correspond to their exemplary, respective sequences.

In particular embodiments, a library is comprised of peptides of a certain length that correspond to their respective antigens, although in some cases a library is comprised of a mixture of peptides with two or more different lengths. The peptides may be of a certain length(s) and they may overlap in sequence of a certain amount, although there may be variability of length of overlap in some libraries. In particular embodiments, the peptides are at least 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example. In particular embodiments, there is overlap among the peptides of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length, for example. In specific embodiments, the peptides are 15 amino acids long and overlap one another by 11 amino acids. A mixture of different peptides may include any ratio of the different peptides, although in some embodiments each particular peptide is present at substantially the same quantities in the mixture as another particular peptide. Although coverage of an antigen in sequence for the peptides may be random and substantially even over a given region of an antigen, in some embodiments a library may be enriched for one or more particular peptides, such as one or more peptides that are known to encode an epitope or a part thereof, for example.

In particular embodiments, the pepmix for a particular antigen protein comprise all possible HLA class I epitopes that are 8 to 10 amino acids long, for example. In specific embodiments, longer peptides are utilized to cover all class II epitopes for a particular peptide. In some cases, a range of length of epitopes is 12-25 amino acids.

II. Methods of Producing and Using Therapeutic VSTs

A. Producing Therapeutic VSTs

In certain aspects, the present disclosure concerns the development of VSTs that target one or more antigens from at least one of EBV, CMV, adenovirus, vaccinia virus, and/or VZV.

In methods of producing the T-cells, peripheral blood T-cells are initially stimulated with APCs that have been exposed to one or more peptides that span some or all of at least one viral antigen. The antigenic peptides may be provided to the APCs as a library of peptide mixtures, and multiple libraries of pepmixes may be provided to the same collection of APCs. In some embodiments, the collection includes both immunodominant and subdominant antigens.

In embodiments of the disclosure, therapeutic T-cells are generated and may be provided to an individual that has a viral infection or is at risk of having a virus-associated medical condition that results indirectly or directly from a viral infection or are provided to an individual that has a non-virally infected tumor. In methods of producing the therapeutic T-cells, under certain conditions peripheral blood T-cells are mixed with APCs that are loaded with a library of peptides that span part or all of one or more viral antigens from one or more viruses. In specific embodiments, for the stimulating step the T-cells reside within a population of PBMCs.

Thus, although the source of the peripheral blood T-cells may be of any kind, in specific embodiments the source is PBMCs, and in some cases a plurality of PBMCs are utilized in the methods, wherein the plurality comprises the peripheral blood T-cells. Peripheral blood T-cells may be isolated or purified at least in part from PBMCs. In some cases, the PBMCs are non-adherent, and in some cases the PBMCs are CD45RA-depleted (wherein the depletion occurs prior to exposure of the PBMCs to the APCs). In specific embodiments, the peripheral blood T-cells have reduced numbers of CD45RA-positive cells in comparison to a normal standard. The peripheral blood T-cells or PBMCs may be depleted for certain cells by using standard means in the art including, for example, magnetic labeling and separation (for example, using Miltenyi® Biotec columns or StemSep™ magnetic beads). The term "depleted" as used herein refers to the peripheral blood T-cells or PBMCs having substantially no CD45RA-positive cells therein. In some cases, "depleted" refers to there being a reduction of a certain percentage of CD45RA-positive cells compared to the numbers of those cells in an original collection of peripheral blood T-cells or PBMCs. The number of CD45RA-positive cells are reduced from an original collection of peripheral blood T-cells or PBMCs because they are manipulated specifically to remove CD45RA-positive cells. In some cases, there is at least a 85%, 86%, 87%, 88%, 89%, 90%, 91%, 92%, 93%, 94%, 95%, 96%, 97%, 98%, or 99% reduction of CD45RA-positive and/or CD45RO-positive cells from an original collection of peripheral blood T-cells or PBMCs following manipulation of the original collection to remove the CD45RA-positive cells. In some embodiments, myeloid cells may be removed using magnetic beads or plastic adherence.

In some embodiments, there is a method of generating T-cells that target at least one antigen from EBV, CMV, adenovirus, Vaccinia, and/or VZV, and this occurs generally by contacting a plurality of PBMCs with a plurality of APCs loaded for peptides from a library of peptides that correspond to one or more particular viral antigens from EBV, CMV, adenovirus, Vaccinia, and/or VZV. In specific embodiments, the exposure of the two populations of cells allows for expansion of the T-cells. In particular embodiments, the stimulation step(s) occurs in the presence of one or more particular cytokines. In certain embodiments, the one or more cytokines are IL-7 and/or IL-15, although in alternative embodiments the cytokine(s) are selected from the group consisting of IL-2, IL-15, IL-7, IL-21, IL-12, IL-6, IL-4, and a combination thereof. In specific embodiments, one or more steps of the methods do not occur in the presence of IL-2, IL-4, IL-6, IL-7, IL-12, and/or IL-21, although alternatively IL-2, IL-4, IL-6, IL-7, IL-12, and/or IL-21 may be utilized. Reference to the presence of a cytokine is to presence of exogenously added cytokine, i.e. excluding any cytokine present within or secreted by the culture of cells. In some embodiments, the peptides are further defined as peptides that overlap in sequence to span part or all of a viral antigen that is not a HPV antigen. For example, in certain aspects the peptides overlap by at least 10 amino acids, and particularly 11, and in some embodiments the peptides are at least 12 or more amino acids in length, and particularly 15 amino acids in length.

The selection of an appropriate amount or concentration of a given cytokine for inclusion in a cell culture is within the ability of the person or ordinary skill in the art. By way of example, the following is a list of certain interleukins and examples of appropriate concentrations that may be used:

Interleukin 6 (IL-6): 50 to 150 ng/ml, one of about 50 ng/ml, 60 ng/ml, 70 ng/ml, 80 ng/ml, 90 ng/ml, 100 ng/ml, 110 ng/ml, 120 ng/ml, 130 ng/ml, 140 ng/ml or 150 ng/ml;

Interleukin 7 (IL-7): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml;

Interleukin 12 (IL-12): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml;

Interleukin 15 (IL-15): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml.

Table 1 below provides examples of certain embodiments of methods of the disclosure.

TABLE 1

Examples of Elements of a Method

| Embodiments | Examples for Embodiments |
|---|---|
| Source of T-cells | Leukapheresis product<br>Apheresis product<br>Peripheral blood mononuclear cells (PBMC)<br>Non-adherent PBMC<br>CD45RA-depleted PBMC<br>Depleted of myeloid cells |
| Antigen-presenting cells (APC) for first stimulation | Dendritic cells (DC)s or PBMCs or monocytes |
| Cytokines for first stimulation (stim) | Combinations of IL15, IL-7, IL21, IL12, IL-6, IL-4 (although in specific embodiments IL-4 is not utilized) |
| Antigen | Viral pepmixes for EBV, CMV, adenovirus, vaccinia, and/or VZV |
| APCs for 2nd stim | DC<br>PBMCs<br>Autologous activated T-cells (AATC) + HLA-negative costimulatory cells |
| APCs for 3rd and subsequent stims | Px-AATCs + HLA-negative costimulatory cells |
| Costimulatory cells | K562 expressing CD86, 4-1BB-L, CD83 and CD80<br>Or HLA-negative Lymphoblastoid cell lines (LCL) |

Thus, in particular embodiments, a population of T-cells (wherein the population may comprise some, a majority, or substantially all T-cells or wherein the population of T-cells is within another population of cells, such as within PBMCs) is exposed to a population of APCs to generate T cell lines having particular characteristics, including at least: a) effectiveness at targeting viral antigen(s); b) polyclonality; c) TH1 bias; d) minimally differentiated memory type; or e) a combination thereof. In specific embodiments, the cells may be minimally differentiated, but in some cases they may not all be and a majority may be somewhat differentiated.

In some cases, T-cells are stimulated more than once, and different stimulation steps may or may not expose the population of cells to the same conditions. In specific embodiments, a first stimulation has conditions different from a subsequent stimulation, including a second stimulation and/or a third stimulation. In specific embodiments, a first stimulation step of the method utilizes APCs that are pepmix-loaded DCs or pepmix-loaded PBMCs and utilizes IL-7 and IL-15, although in alternative embodiments the step utilizes one or more cytokines selected from IL15, IL-7, IL21, IL12, IL-6, and/or IL-4. This stimulation step may optionally be repeated one or more times.

In certain embodiments of the methods, between days 8 and 10 following an initial exposure of the peripheral blood T-cells (or PBMCs) to the pepmix or APCs, there may be a re-stimulation of the PBMCs on day 8, day 9, or day 10, but rarely later, and then a subsequent re-stimulation may occur on day 15, day 16, or day 17 (see FIG. 7 as an example of one specific embodiment).

In some cases, a stimulation step that is subsequent to the first stimulation step (including optional repeats of the first stimulation step), the resultant T-cells obtained after the first stimulation (and which may reside in a heterogeneous population of cells) may be exposed to pepmix-loaded DCs or pepmix-loaded PBMCs and/or pepmix-pulsed autologous activated T-cells and/or HLA-negative costimulatory cells. Generally sufficient cells are produced after a second stimulation on day 8 to 10 with pepmix-pulsed AATCs combined with HLA-ve costimulatory cells. Occasionally a third stimulation may be required using the same antigen-presenting complex. Costimulatory cells that may be utilized in any stimulation step include at least cells that express CD86, 4-1BB, and/or CD83 and/or cells that are HLA-negative lymphoblastoid cells. In specific cases, the costimulatory cells may be gene-modified K562 cells.

In some embodiments, during the steps of the method the cells in culture are modified. In specific embodiments, the cells are modified to harbor a polynucleotide that expresses a gene product that renders the cells effective or more effective for a specific purpose or function, such as effective or more effective for targeting a particular target and/or enhanced in function for T-cell-mediated cytotoxicity, for example. In specific embodiments, the cells are modified to express a certain non-natural receptor that allows the T-cells to effectively or more effectively target a desired target cell, such as one that expresses a certain antigen. In specific embodiments, the cells are modified to express a chimeric antigen receptor (CAR), and so forth. The cells may be modified to express an expression vector (that may be viral (including retroviral, lentiviral, adenoviral, adeno-associated viral, and so forth) or non-viral, e.g., a transposon such as piggyBac) during the method at specific time points, such as the vector being introduced between day 2 and 5 of culture, for example so that the vector is expressed in T-cells with long-term repopulation potential. In specific embodiments the cells are exposed to the expression vector within about 3 days after each stimulation, but in such cases the modification occurs in more differentiated T-cells that have less long term potential (which in specific circumstances is desirable, such as if long term expression of gene-modified cells is not desirable, as in the case where the transgene has potential toxicity, for example).

In specific embodiments, the cells are modified to express a CAR that targets a cancer antigen, such as EphA2, HER2, GD2, Glypican-3, 5T4, 8H9, $\alpha_v\beta_6$ integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor a, GD2, GD3, HLA-AI MAGE A1, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC1, PSMA, ROR1, Sp17, SURVIVIN, TAG72, TEM1, TEM8, VEGRR2, carcinoembryonic antigen, HMW-MAA, VEGF receptors, and/or other exemplary antigens that are present with in the extracellular matrix of tumors, such as oncofetal variants of fibronectin, tenascin, or necrotic regions of tumors and other tumor-associated antigens or actionable mutations that are identified through genomic analysis and or differential expression studies of tumors, for example.

B. Using Therapeutic VSTs

In certain embodiments, cells produced by methods of the disclosure are provided to an individual in need thereof for treatment of a medical condition or to target a viral infection or virus-associated cancer or non-virus-associated cancer in which no symptoms of a medical condition are detectable or have manifested. As used herein "treatment" or "treating," includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

In the methods encompassed by the disclosure, the therapeutic T-cells are utilized to treat virus-associated disease caused directly or indirectly by a single non-HPV virus or are otherwise provided to an individual that is seropositive for a single non-HPV virus. In other cases, the therapeutic T-cells are utilized to treat disease(s) caused directly or indirectly by more than one virus In the collection of therapeutic T-cells, each T-cell and its progeny has specificity for only one peptide in one antigen from one virus, and upon production of the collection of therapeutic T-cells, one expands a population of T-cell clones that together have multi-specificity, such as for multiple epitopes in each viral antigen, for example.

In at least some methods of the disclosure, a therapeutically effective amount of the VSTs generated thereby are administered to an individual, for example, an individual known to have or suspected of having or susceptible to having disease associated with EBV, CMV, adenovirus, vaccinia virus, and/or VZV. In specific embodiments, the cells are administered by injection, such as intravenous, intramuscular, intradermal, subcutaneous, intraperitoneal injection, and so forth, for example. In some embodiments, the VSTs may be polyclonal CD4+ and CD8+ VSTs. The PBMCs may be allogeneic to the individual or are autologous to the individual.

In certain cases, neoplasms are treated with cells of the disclosure, and the neoplasm may be benign, malignant, or a premalignant lesion that can lead to cancer. Thus, an individual may be treated with cells produced by methods of the disclosure at the premalignant lesion stage and/or after the lesion becomes malignant. The individual may have early or late stage cancer, and the skilled artisan is aware that the methods of producing the cells may be tailored for such different stages of cancer, such as by utilizing peptides for the APCs that are from antigens associated with early vs. late stage cancer. In specific embodiments, the cancer may be primary, metastatic, recurrent, refractory, and so forth.

In some cases, one can determine the virus or viruses that are associated with the medical condition before administration of the cells, although in some cases the virus type(s) is not determined. In specific embodiments, cells specific for EBV, CMV, adenovirus, vaccinia virus, and/or VZV have activity for individuals that are positive for EBV, CMV, adenovirus, vaccinia virus, and/or VZV, respectively. In some cases cells specific for one of the viruses encompassed herein are gene-modified with a receptor for a non-viral tumor and then infused to treat that non-viral tumor, so that the virus or viral antigen can be used to stimulate expansion of the T-cells in vivo, for example by vaccination or using oncolytic viruses or endogenous viruses.

In cases wherein the APCs of the stimulation steps of the method are loaded with pepmixes of different viral antigens together, the outcome of administration of T-cells expanded through such APCs is determined by whether the individual has been exposed to the virus. For example, in particular embodiments if an individual is infected with a certain virus, only T-cells specific for that virus will respond, and this is because the infection will initially have stimulated a T-cell response to that virus. Those T-cells will expand in the individual and then become memory T-cells and would be at higher numbers than T-cells specific for another virus that have never been activated.

The individual being treated may be known to have a virus-associated disease, suspected of having a virus-associated disease, or at risk for a virus-associated disease. An individual being treated may have the presence of the virus but there are not yet any deleterious symptoms of a virus-related medical condition. The individual may be at risk for a non-HPV virus-associated disease given an environment or event that exposes them to the non-HPV virus.

In some embodiments, one or more administrations of the cells produced by methods of the disclosure are provided to an individual in need thereof. The length of time between multiple administrations may be of any suitable duration so long as subsequent administrations are effective against the cancer, including on the order of days, weeks, months, or years. In cases wherein more than one administration of cells are provided to the individual, the antigen to which the cells are targeted may or may not be the same antigen as the cells utilized in earlier administration(s). For example, in a first administration of cells, they may target one viral antigen, whereas in another administration of cells, the cells target a different antigen, including from a different virus, in at least some cases.

In some cases, an individual is optionally determined to have viral infection by any suitable means in the art. One may employ infection diagnosis methods such as DNA tests utilizing PCR, Southern blot hybridization, in situ hybridization, and these methods may or may not be used in conjunction with other methods, for example.

In specific embodiments, the individual is immunocompromised (which for example, may be defined as an individual whose ability to fight infectious disease or cancer with the immune system is compromised or entirely absent). In specific embodiments, the immunocompromised individual has had a stem cell transplant (including hematopoietic stem cell transplantation), has had an organ transplant and/or has received one or more cancer treatments, including chemotherapy or radiation, or has been infected with HIV, for example. In some cases, the individual has acquired or inherited immune deficiency disorder. In some embodiments, those that are immunocompromised by their disease and/or its treatment are provided methods and/or compositions of the disclosure.

A. Epstein-Barr Virus

The Epstein-Barr virus (EBV), also called human herpesvirus 4 (HHV-4), is one of eight known viruses in the human Herpesviridae family EBV causes infectious mononucleosis, some forms of cancer (including Hodgkin's lymphoma, Burkitt's lymphoma, gastric cancer, nasopharyngeal cancer, NK/T lymphoma, diffuse large B-cell lymphoma, and leiomyosarcoma, at least), and certain conditions associated with human immunodeficiency virus (HIV), including hairy leukoplakia and central nervous system lymphomas, as examples. In methods of the disclosure, EBV infection or one or more EBV-associated medical conditions are treated using the cells.

Although EBV encodes about 90 proteins, a limited fraction of these are expressed in EBV-associated malignancies. About 80 genes are involved in the viral lytic cycle and about 9 genes are associated with virus latency. In some tumors only 4 EBV genes are expressed and in others only 2 are expressed. Recently some tumors have been show to undergo abortive virus replication and express early viral proteins and they have also been show to express unexpected transcripts from the lytic cycle. All of these provide transcripts may encode potential target antigens for VSTs. Generally one can target LMP1, LMP2, BARF1 and EBNA1 that are considered EBV type 2 latency antigens. However, in some cases one may also target early viral proteins, such as those encoded by BZLF1, BRLF1, BMLF1 or unexpected transcripts such as BXLF1/2, for example.

B. Cytomegalovirus

Cytomegalovirus (CMV), also known as human herpesvirus-5, is a virus in the family Herpesviridae. CMV infection normally does not result in disease unless the infected individual is an infant or is immune-compromised (such as an organ or tissue or cell transplant recipient, including after allogeneic marrow transplantation, for example). Although any antigen of CMV may be targeted with cells produced by methods of the disclosure, in specific embodiments the antigen is the immediate early antigen, IE1, and the tegument protein, pp65.

C. Adenovirus

Adenoviruses can cause common cold, sore throat (pharyngitis), bronchitis, pneumonia, diarrhea, pink eye (conjunctivitis), fever, cystitis, gastroenteritis, and neurologic disease. Healthy individuals are rarely subject to adenovirus-associated serious illness or death. However, infants and people with weakened immune systems, or existing respiratory or cardiac disease, are at higher risk of developing severe illness from an adenovirus infection.

Cells of the disclosure may be targeted for any adenovirus antigen, but in specific embodiments the antigen is hexon and/or penton.

D. vaccinia Virus vaccinia virus (also called VACV or VV) is a poxvirus that causes cow pox in cows but has provided an effective vaccine for smallpox, which may be treated with cells produced by methods of the disclosure. Although any antigen of vaccinia virus may be targeted with cells produced by methods of the disclosure, in particular cases the antigens are E3L, A10L/121L, H3L/093L, G5R/074R, C7L/018R, B22R/189R, DBL, ESR, E4L, f17R, A17L, and/or L4R.

E. Varicella Zoster Virus

Varicella zoster virus (VZV) is one of eight herpesviruses known to infect humans and vertebrates. VZV causes chickenpox in children, teens and young adults, and it causes herpes zoster (shingles) in adults and some children. VZV is known by many names, including chickenpox virus, varicella virus, zoster virus, and human herpesvirus type 3 (HHV-3).

VZV antigens that may be utilized as a source of peptides (or sequence thereof) include any of the capsid, envelope, or soluble antigens. Specific examples include V antigen, S antigen, 1E61, 1E62, 1E63, gE and ORF10.

Vaccines for VZV (VARIVAX® and ZOSTAVAX®) comprise live attenuated viruses that cause limited infection in humans.

III. Pharmaceutical Compositions

In accordance with this disclosure, the term "pharmaceutical composition" relates to a composition for administration to an individual. In a preferred embodiment, the pharmaceutical composition comprises a composition comprising therapeutic immune cells for parenteral, transdermal, intraluminal, intra-arterial, intrathecal or intravenous administration or for direct injection into a cancer. It is in particular envisaged that the pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, and the cells may be in a sterile buffer suitable for infusion with a protein such as human serum albumin for infusion.

The dosage regimen will be determined by the clinical protocol that has been approved by the appropriate local and federal regulatory agents. As is well known in the medical arts, dosages for any one patient depends upon many factors, including the patient's size and body surface area, for example. A particular dosage for administration might be in the range of from $5\times10^6$ per $m^2$ to $5\times10^9$ per $m^2$. Progress can be monitored by periodic assessment.

In certain embodiments of the disclosure that concern VSTs generated against viral antigen(s), methods of the present disclosure for clinical aspects are combined with other agents effective in the treatment of one or more medical conditions with which the virus is associated.

IV. Kits of the Disclosure

Any of the compositions described herein may be comprised in a kit. In a non-limiting example, a library of pepmixes may be comprised in a kit, any type of cells may be provided in the kit, and/or reagents for manipulation of pepmixes and/or cells may be provided in the kit. Cytokines or means of producing them (such as vectors that encode them) may be included in the kit. Cell culture reagents and/or apparatus(es) may be included. The component(s) are provided in suitable container means.

The kits may comprise a suitably aliquoted compositions of the present disclosure. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

In some cases, reagents and/or devices to detect viral infection may be included in the kit. Examples include swabs, spatulas, cytobrushes, slides, cover slips, cytology sample collection receptacle, and so forth. Additional drugs for viral infection may be included in the kit.

EXAMPLES

The following examples are presented in order to more fully illustrate the preferred embodiments of the invention. They should in no way, however, be construed as limiting the broad scope of the invention.

Example 1

Production of Therapeutic T Cells

In some embodiments of the disclosure, there is a mechanism by which one can rapidly generate a single preparation of T-cells, including polyclonal (for example, CD4+ and CD8+) VSTs, that are consistently specific for a variety of antigens derived from one or more human viruses that can prove fatal. The disclosure is readily adaptable to clinical implementation and can be used as an "off the shelf" antiviral agent, including for EBV, CMV, adenovirus, vaccinia virus, and/or VZV. The methods and compositions are readily adaptable to clinical implementation and are useful as a safe and effective antiviral agent for individuals.

In specific embodiments, peripheral blood T-cells are stimulated with monocyte-derived dendritic cells loaded with pepmixes (peptide libraries of 15-mers overlapping by 11 amino acids (aa)) spanning the antigen protein, in the presence or absence of specific accessory cytokines. The resulting T-cell lines may be further expanded with pepmix-loaded activated cells.

The presence of the cytokines IL-7 and IL-15 is useful, in specific embodiments of the methods. These T-cell lines possess the desirable characteristics of polyclonality, multiple T-cell subset representation (including the memory compartment) and a TH1 bias, and eliminate viral targets. The disclosure provides that it is possible to robustly generate viral-directed T-cell lines from patients with virus-associated cancers. Because the technique is scalable and good-manufacturing procedures-compliant, these lines are useful for adoptive cellular immunotherapy of patients with virus-related medical condition(s).

Turning to specifics of the methods, in certain cases DCs are loaded with viral antigen(s) pepmix libraries. In such cases, the cell lines are able to recognize one or more viral antigens. In at least certain cases, expansion of the T-cells occurs in the presence of IL-7 and IL-15 but not IL-2. The presence of IL-7 and IL-15 in conditions for the method may or may not be at each step of stimulation and expansion. In some embodiments, expansion of the virus-specific T-cells after initial generation/expansion with DCs utilizes autologous, polyclonal activated T-cells loaded with pepmixes, in the presence of costimulatory cells (CD80/CD86/CD83/4-1BBL or others), and IL-7 and IL-15. Employing these conditions, T-cell expansion occurs at a more rapid rate than in the absence of such conditions and occurs without loss of specificity.

Example 2

Generation of Non-HPV Antigen-Specific T-Cells

Turning to particular embodiments of the disclosure, methods for generating antigen-specific immune cells, such as T-cells, that are specific for viruses other than HPV are described herein. In particular embodiments, the method(s) are effective for at least EBV, CMV, adenovirus, VZV, vaccinia virus, HIV, BK and HHV6, although the methods may be effective for other viruses. Modifications of these methods compared to those known in the art address deficiencies, such as low frequency of viral-specific antigen-specific T-cells and/or high frequency of NK cells in some viral-specific antigen-specific T cell lines, for example.

In the first stimulation, in specific embodiments there are no DCs, as with other methods in the art. PBMCs utilized as a source of T-cells in steps of the method may be depleted for certain cells, such as depletion of CD45RA+ cells, for example.

Culture of the cells at any step of the method may occur in the presence of certain cytokines or combinations thereof, and certain levels of these cytokine(s) may need to be achieved. In specific embodiments, one or more steps of the method occurs in high (100 ng to 1000 ng per mL) doses of IL15 and IL-7. In specific cases, in one or more steps of the method costimulatory cells are utilized. Although a variety of costimulatory cells may be useful, in specific embodiments the cells are HLA-negative LCLs.

Figure 1:
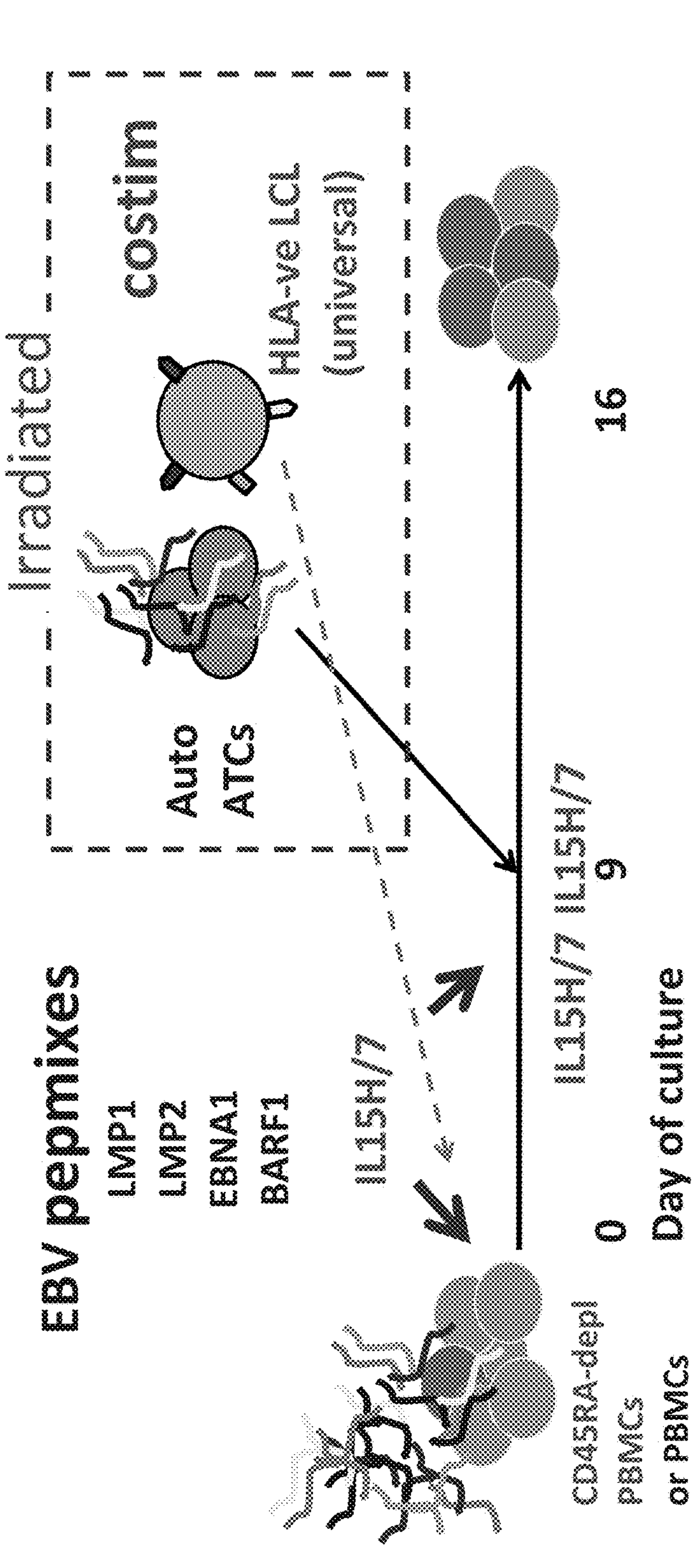
FIG. 1 illustrates general embodiments of virus-specific T-cell (VST) generation methods of the disclosure.

FIG. 1 describes steps of the methods of the disclosure for generating virus-specific T-cells. As illustrated therein, on day 0 PBMCs (which may or may not be depleted for certain cells, such as CD45RA+ T-cells), are pulsed with viral peptides; as an example for EBV, peptides that encompass part or all of LMP1, LMP2, EBNA1, and/or BARF1 are utilized. In this first step where PBMCs of any kind are pulsed with peptides, there may be present cytokines, including certain one or more cytokines, including certain combinations of cytokines. As an example, in the original pulse step, IL7 and/or IL15, including human IL15 (IL15H), are employed. In this first step, there may or may not also be costimulatory cells, including irradiated HLA-ve LCLs. In a second stimulation, the cells are exposed to peptide-pulsed irradiated autologous antigen T-cells and in at least some cases also costimulatory cells, such as HLA-ve LCLs. This step may or may not occur in the presence of one or more cytokines, including certain combinations, such as IL7 and/or IL15, including IL15H. Following continued culturing for an appropriate time span, such as number of days, the cells may be used or may be cryopreserved.

As noted above, embodiments of the disclosure provide improvements to certain methods utilized in the art. FIG. 2 shows results of improved specificity of EB viral-specific T-cells (EBVSTs) developed in the presence of IL-7 and IL-15 instead of IL-4 and IL-7.

Figure 3:
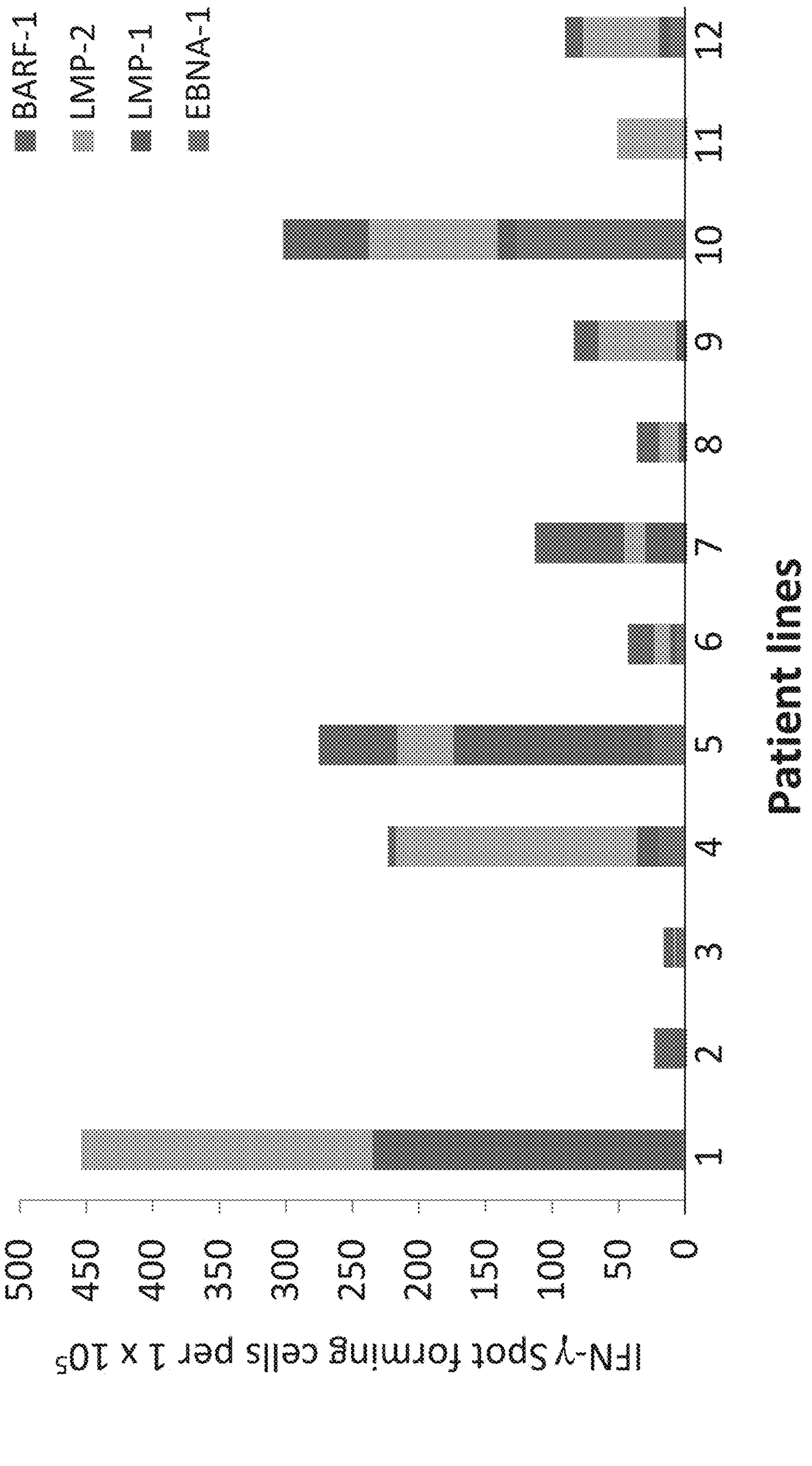
FIG. 3 shows improved specificity of lymphoma patient EBVSTs grown in the presence of IL-7 and IL-15.
Figure 4:
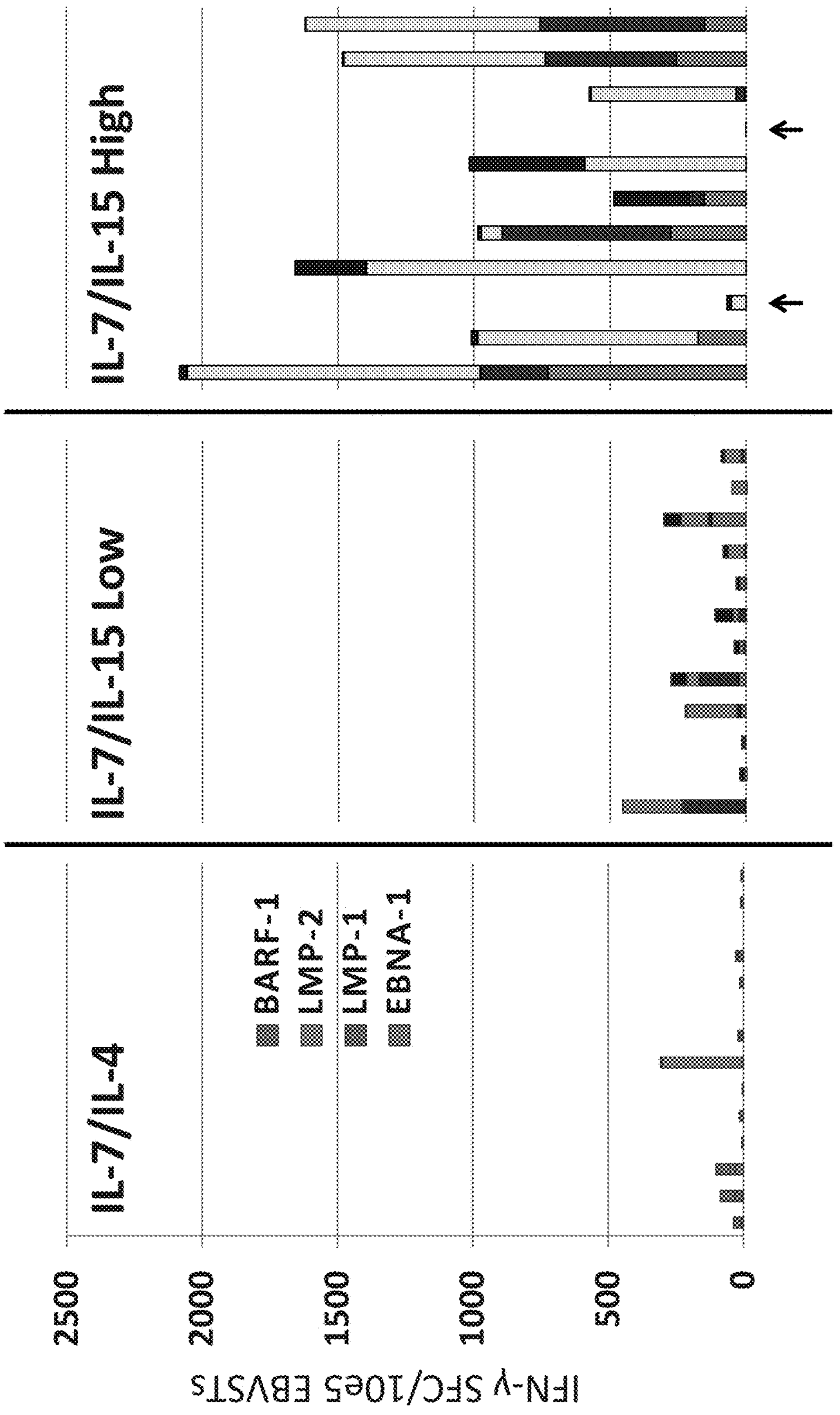
FIG. 4 demonstrates that high doses of IL-15 increase specificity of VSTs.
Figure 5:
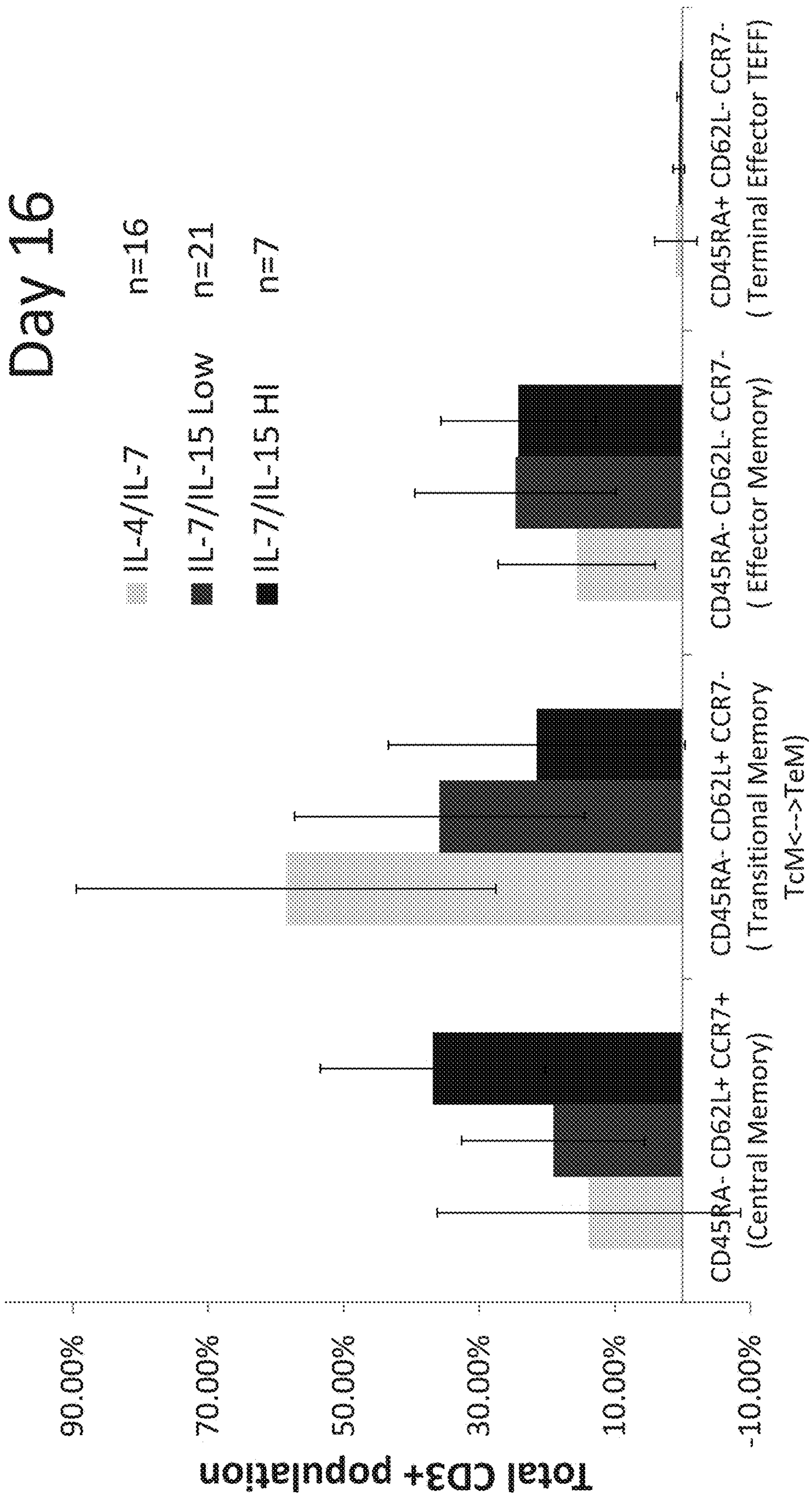
FIG. 5 shows that high dose of IL-15 increases central memory EBVSTs.

As merely an example, methods of the disclosure are developed for lymphoma patients, whose T-cells are anergic to viral antigens expressed in their tumor cells. Specific embodiments of methods of the disclosure improve the antigen-specificity of lymphoma patient EBVSTs and allow anergy to be overcome by utilizing at least IL-15 in one or more steps (FIG. 3). Thus, using IL-15 instead of IL-4 increases the frequency of antigen-specific T-cells in patient EBVSTs. In at least some cases, however, EBVSTs in patients wherein IL-15 had been utilized in culture lacked specificity, so the dosage or IL-15 was optimized. It was questioned whether the IL-15 dose was too high, inducing expansion of non-specific T-cells, for example. In fact, an optimization study (FIG. 4) revealed that a higher dose of IL-15 was better for increasing specificity (100 ng per mL compared to standard dose of 5 ng per mL). FIG. 5 demonstrates that high doses of IL-15 increase central memory EBVSTs.

Figure 6:
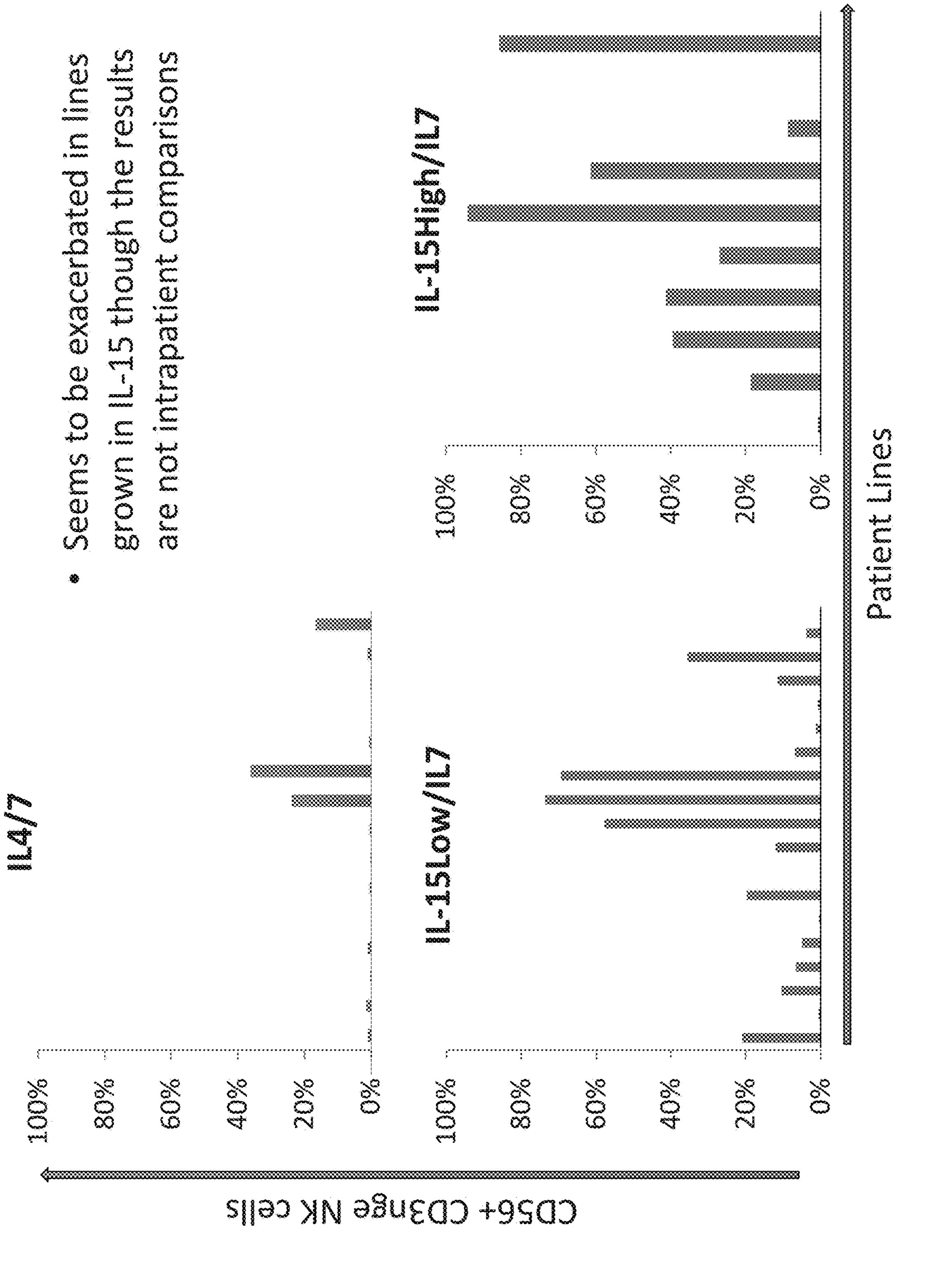
FIG. 6 shows excessive NK-cell outgrowth in EBVSTs from some patients.

Excessive NK cell outgrowth in EBVSTs from some patients and healthy donors was addressed. In cases wherein there is preferential outgrowth of NK cells, in specific cases it could be attributable to the presence of IL-15 (NK cell populations seem to be exacerbated in lines grown in IL-15 and IL-7) and/or could be attributable to the use of K562cs (irradiated HLA-negative K562 cells genetically modified to express CD80, CD83, CD86, and 4-1BBL) (FIG. 6) or the combination of IL15 and K562 cells. To address this, conditions were developed to avoid excessive NK cell outgrowth. In specific embodiments, there was utilized depletion of CD45RA+ cells from the PBMCs prior to T-cell activation. CD45RA is a naïve T-cell marker that is also expressed on natural T-regulatory cells and NK cells, so such depletion should remove the NK cells. In other embodiments, CD45RO-positive cells are enriched through depletion of cells expressing CD45RA. In addition, this step should remove T regulatory cells that can inhibit the outgrowth of antigen-specific T-cells, especially in cancer patients, and also removes naïve cells that can grow as bystander cells and dilute the antigen-specific T-cells. Depletion may occur by any suitable method, but in specific embodiments depletion occurs using magnetic labeling and separation (for example, using Miltenyi® Biotec columns) Use of antibody to deplete cells using magnetic beads or nanobubbles may also occur.

Figure 7:
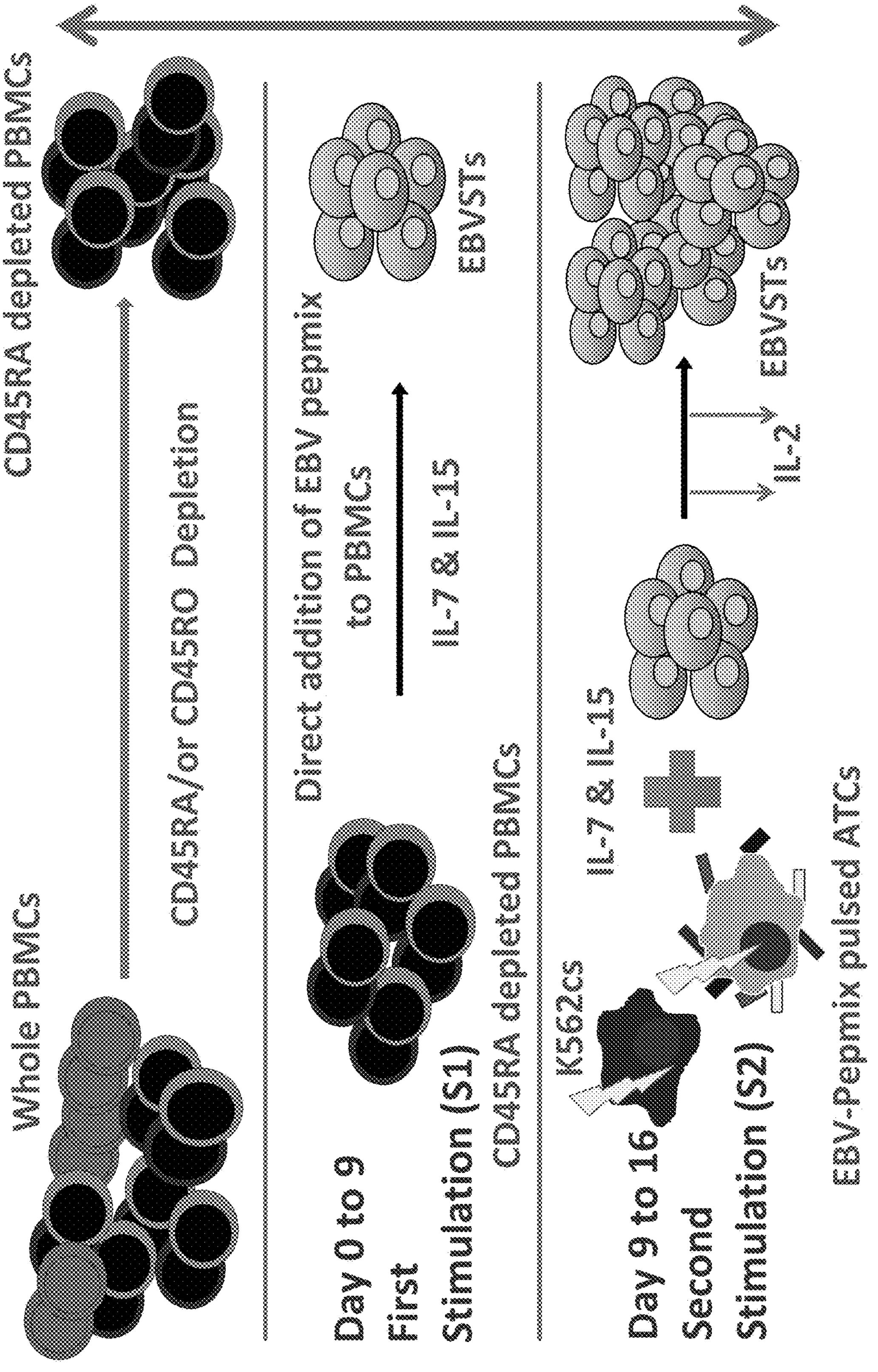
FIG. 7 illustrates generation of pepmix-activated EBVSTs from CD45RA-depleted PBMCs.
Figure 8:
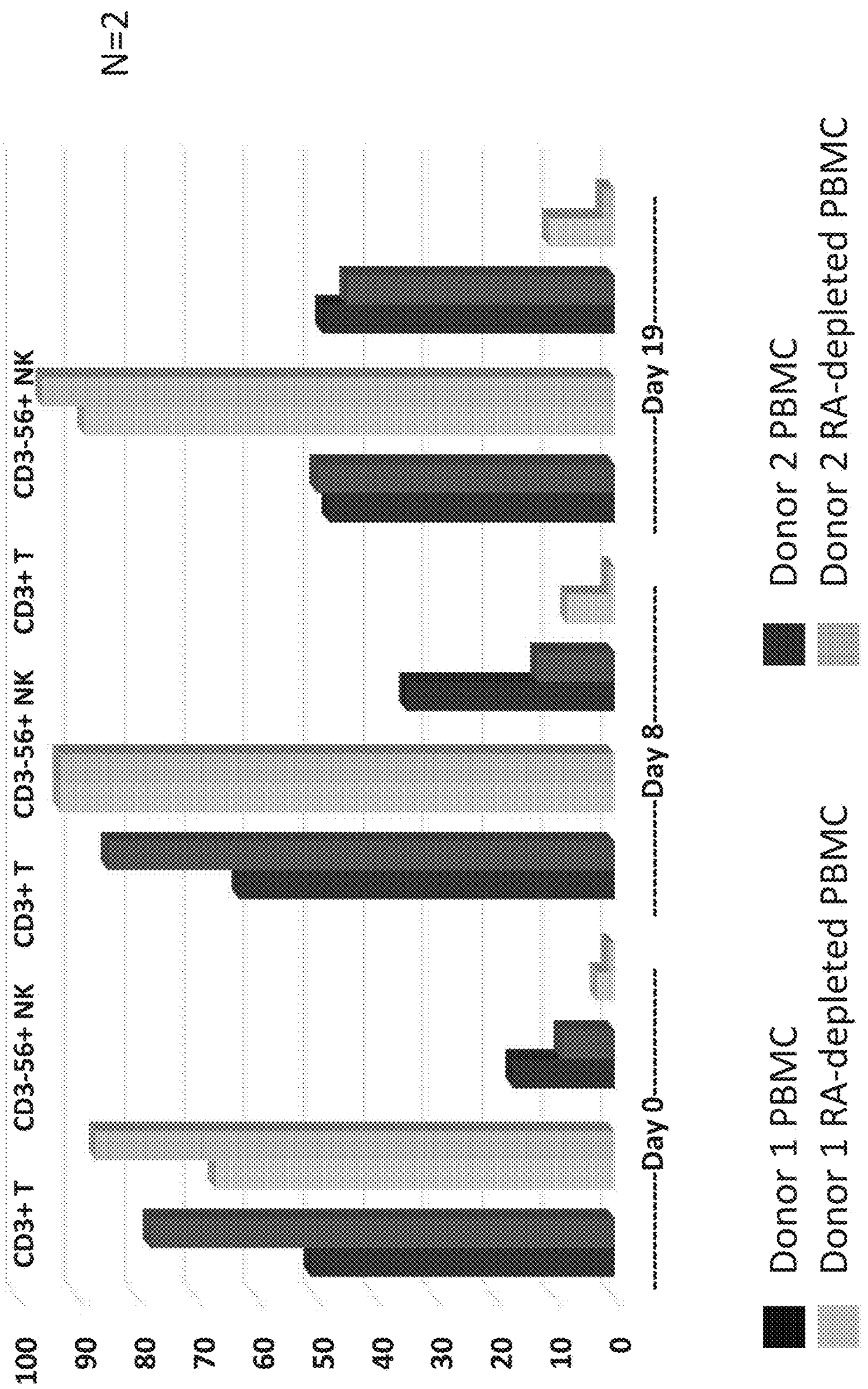
FIG. 8 demonstrates that CD45RA depletion decreases the frequency of CD3-CD56+NK cells in EBVSTs expanded from healthy donors.
Figure 9:
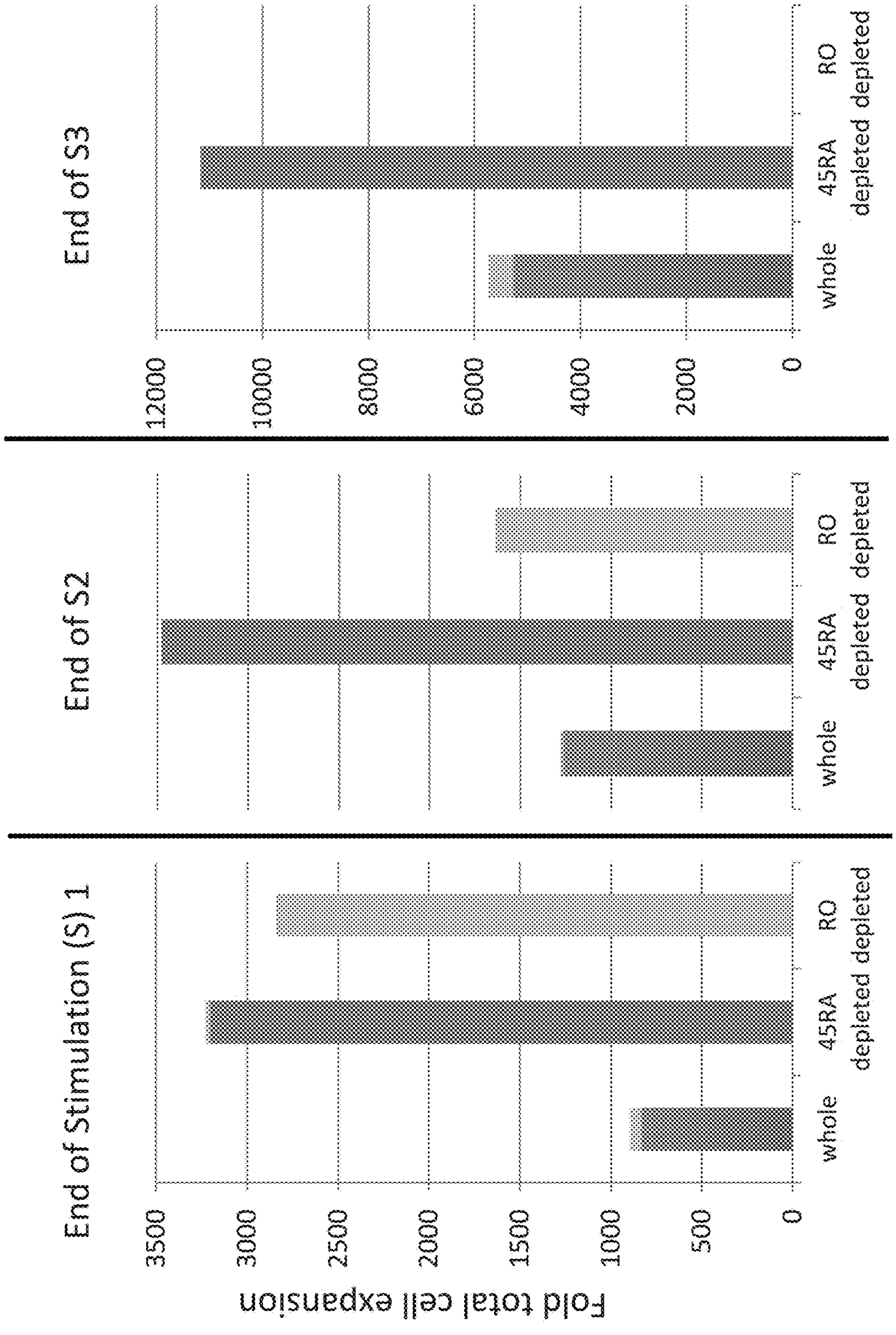
FIG. 9 shows that removal of CD45RA+ cells increases proliferation of EBVSTs.
Figure 10:
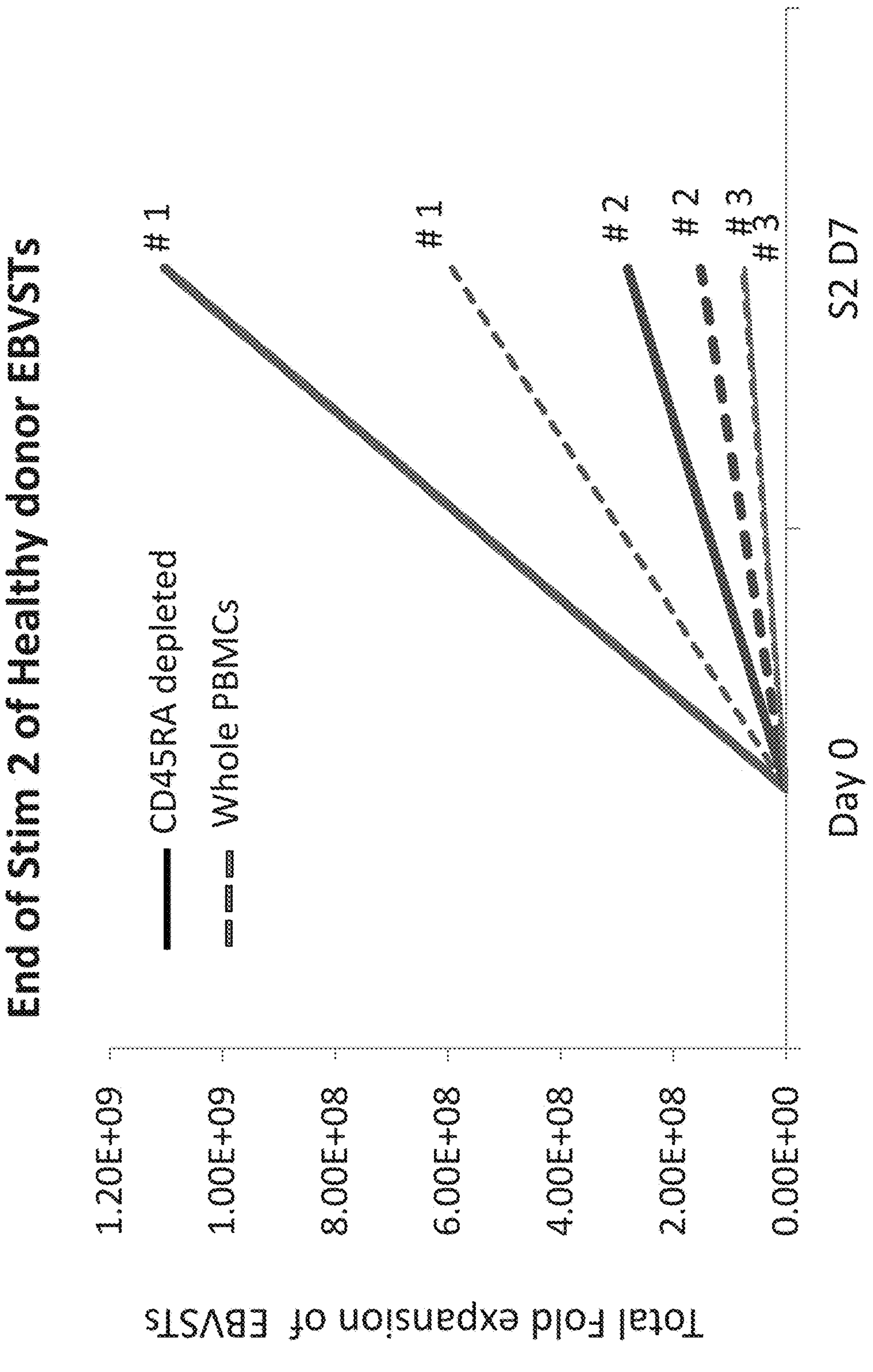
FIG. 10 demonstrates that CD45RA depletion enhanced the fold expansion of EBVSTs.
Figure 11:
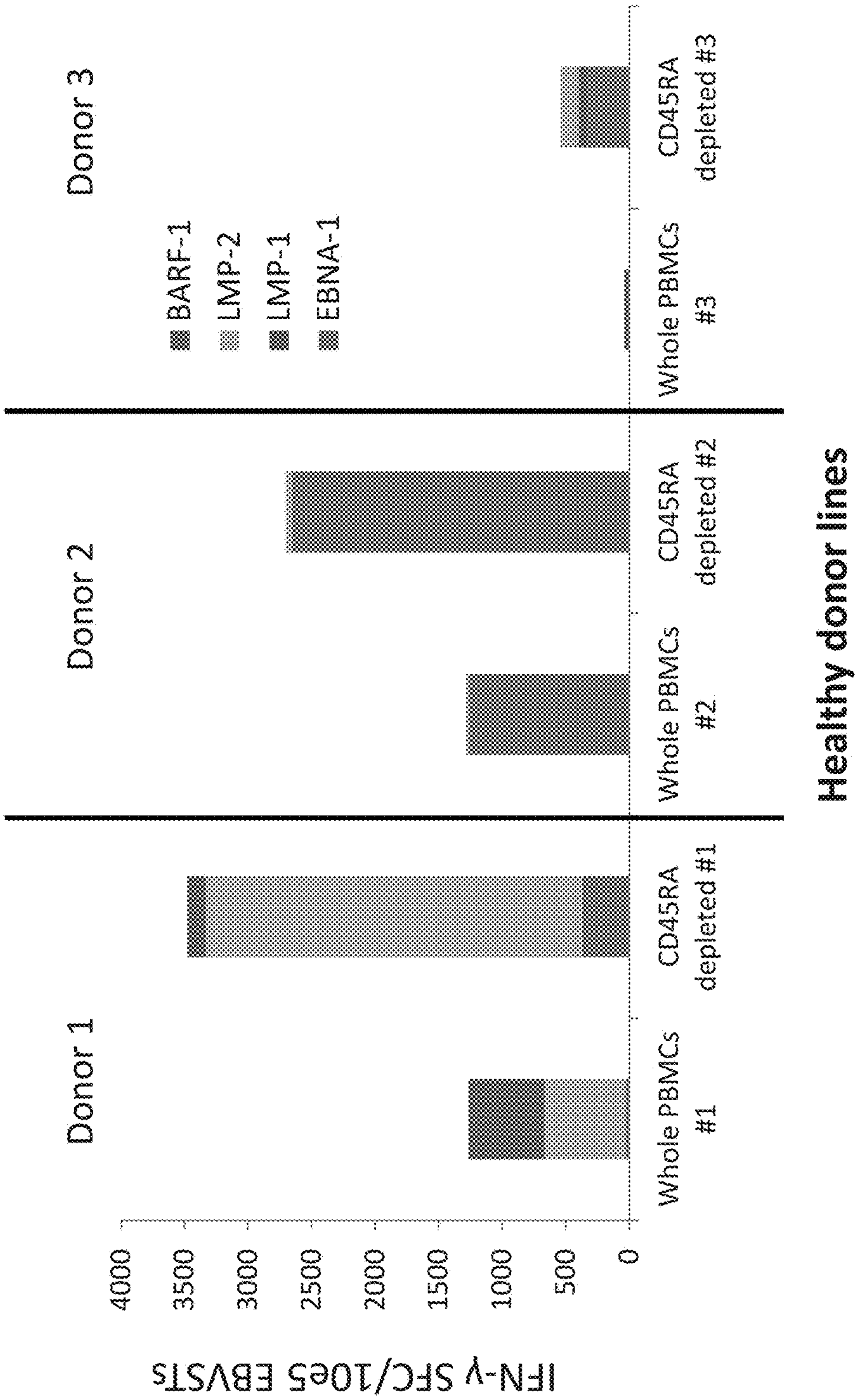
FIG. 11 shows CD45RA depletion enhances antigen specificity of EBVSTs at the end of a second stimulation (at day 16).
Figure 12:
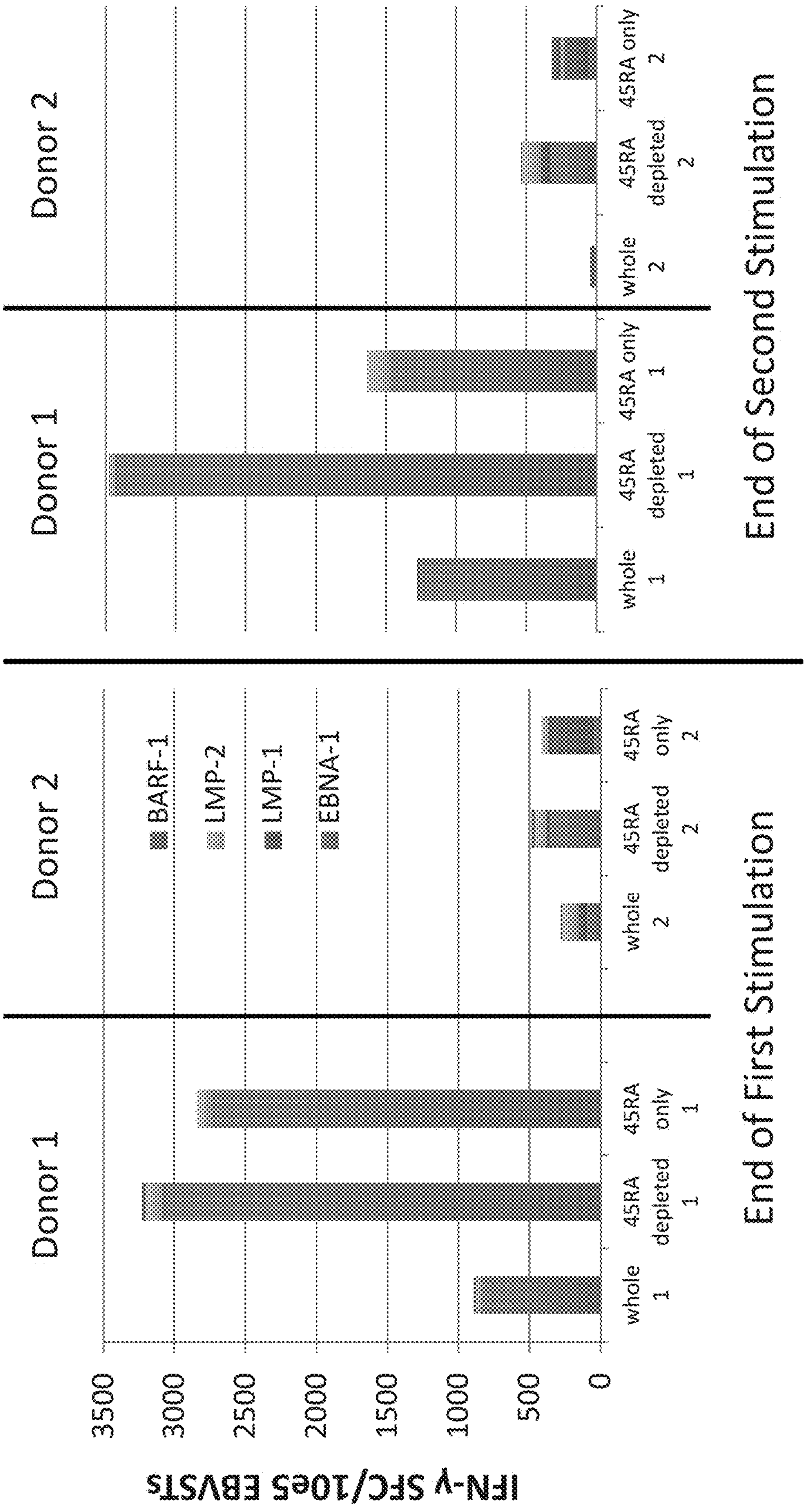
FIG. 12 demonstrates CD45RA depletion enhances antigen specificity of EBVSTs.
Figure 13:
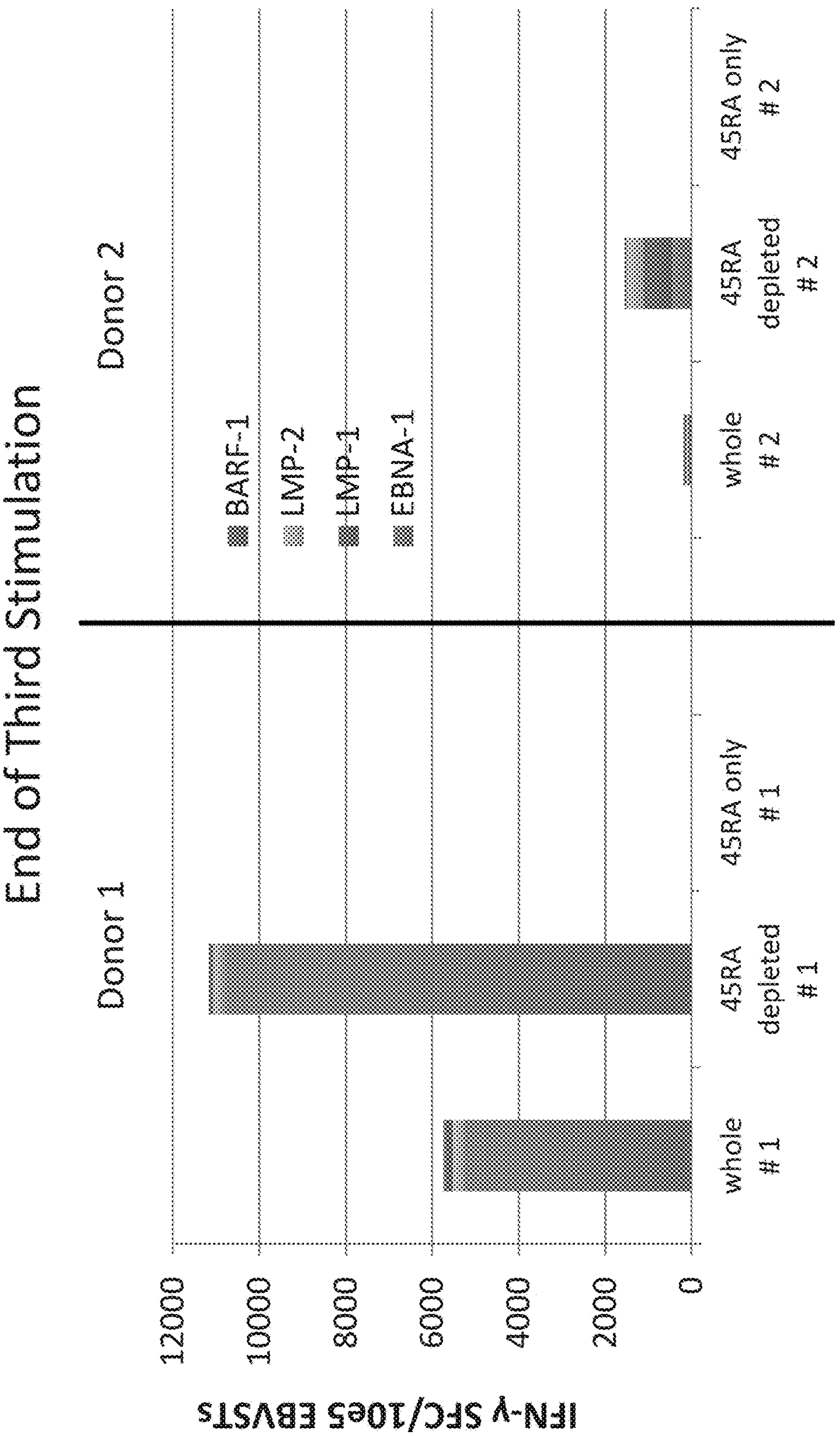
FIG. 13 demonstrates increased antigen specificity of CD45RA depleted EBVSTs sustained after a third stimulation.

Generation of pepmix-activated EBVSTs from CD45RA-depleted PBMCs is illustrated in FIG. 7. As shown therein, whole PBMCs are depleted of CD45RA, and beginning day 0 or dayl the first stimulation (S1) EBVpepmix is added to the depleted cells in the presence of IL-7 and IL-15 to produce EBVSTs. At the end of S1 and beginning of the second stimulation S2 (for example, between day 8 and day 10), the EBVSTs are exposed to sufficient amounts of EBV-Pepmix pulsed ATCs and sufficient amounts of costimulatory cells (such as K562cs cells) in the presence of IL-7 and IL-15, but in the absence of IL-2, to produce the desired pepmix-activated EBVSTs. FIG. 8 demonstrates the results that CD45RA depletion (CD45RA+ PBMC from healthy donors were depleted using Miltenyi® columns and GMP grade CD45RA-conjugated beads) decreases the frequency of CD3-CD56+NK cells in EBVSTs. Following this, there is increased proliferation of EBVSTs (FIG. 9). FIG. 10 illustrates the enhanced fold expansion of EBVSTs following CD45RA depletion from healthy donors at the end of a second stimulation step. In addition, the CD45RA depletion enhances antigen specificity of EBVSTs at the end of a second stimulation (for example, day 16) (FIGS. 11 and 12, both showing data for healthy donors). The increased antigen specificity of CD45RA depleted EBVSTs is sustained after a third stimulation (FIG. 13).

Figure 14:
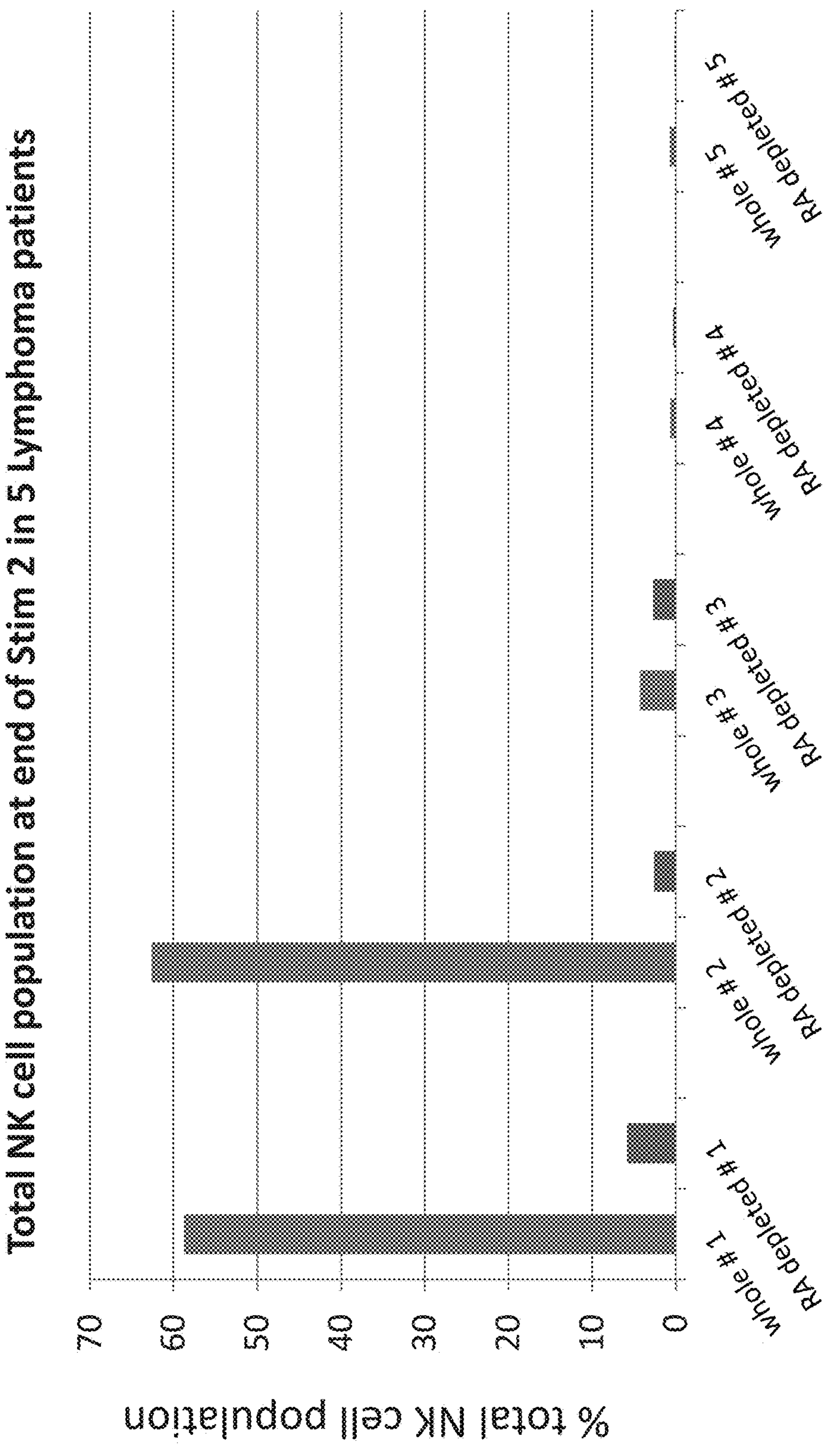
FIG. 14 demonstrates CD45RA depletion decreases NK cell population outgrowth in lymphoma patient EBVSTs.
Figure 15:
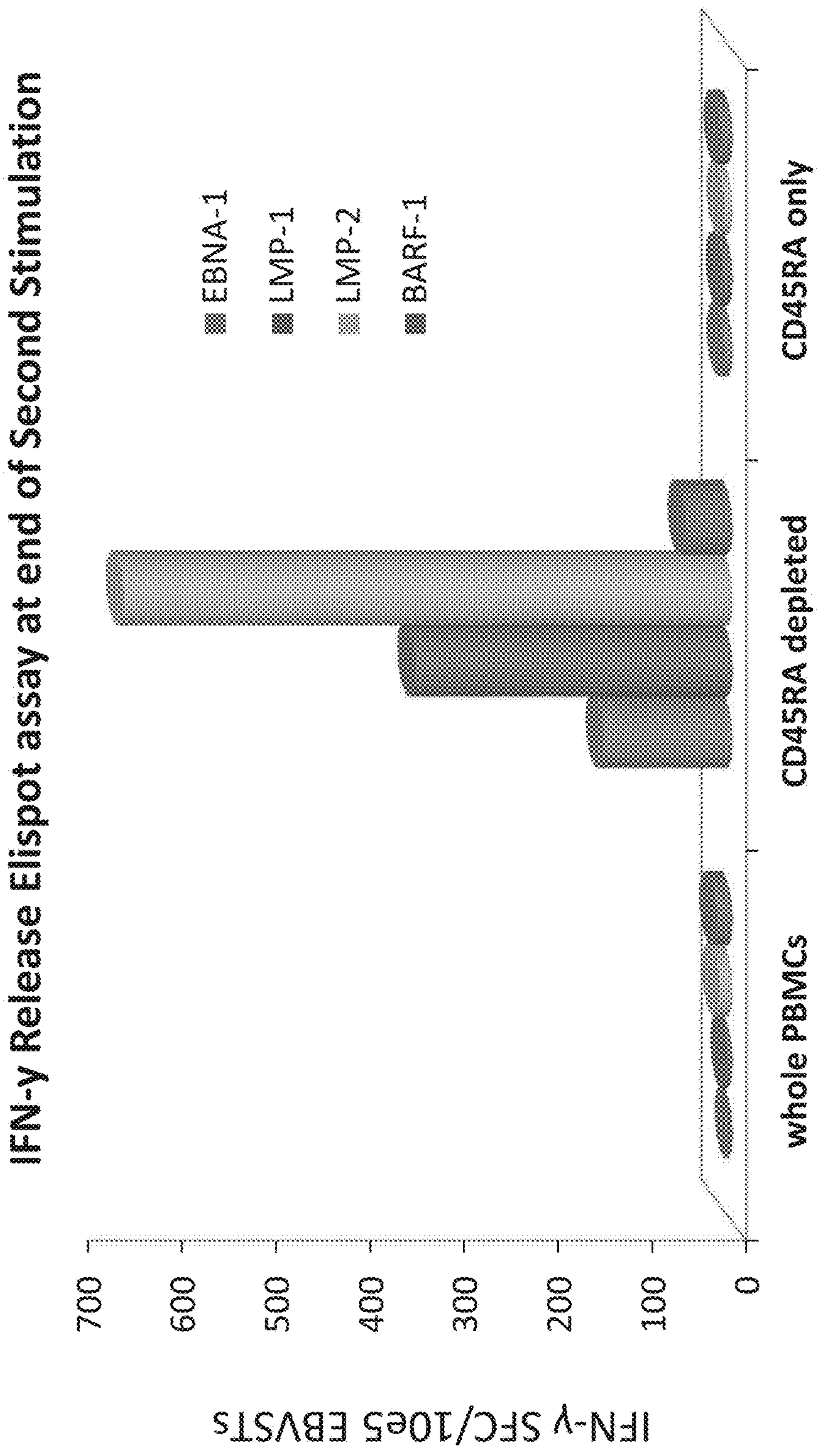
FIG. 15 shows CD45RA depletion increased the frequency of antigen specific T-cells in lymphoma patient EBVSTs.
Figure 16:
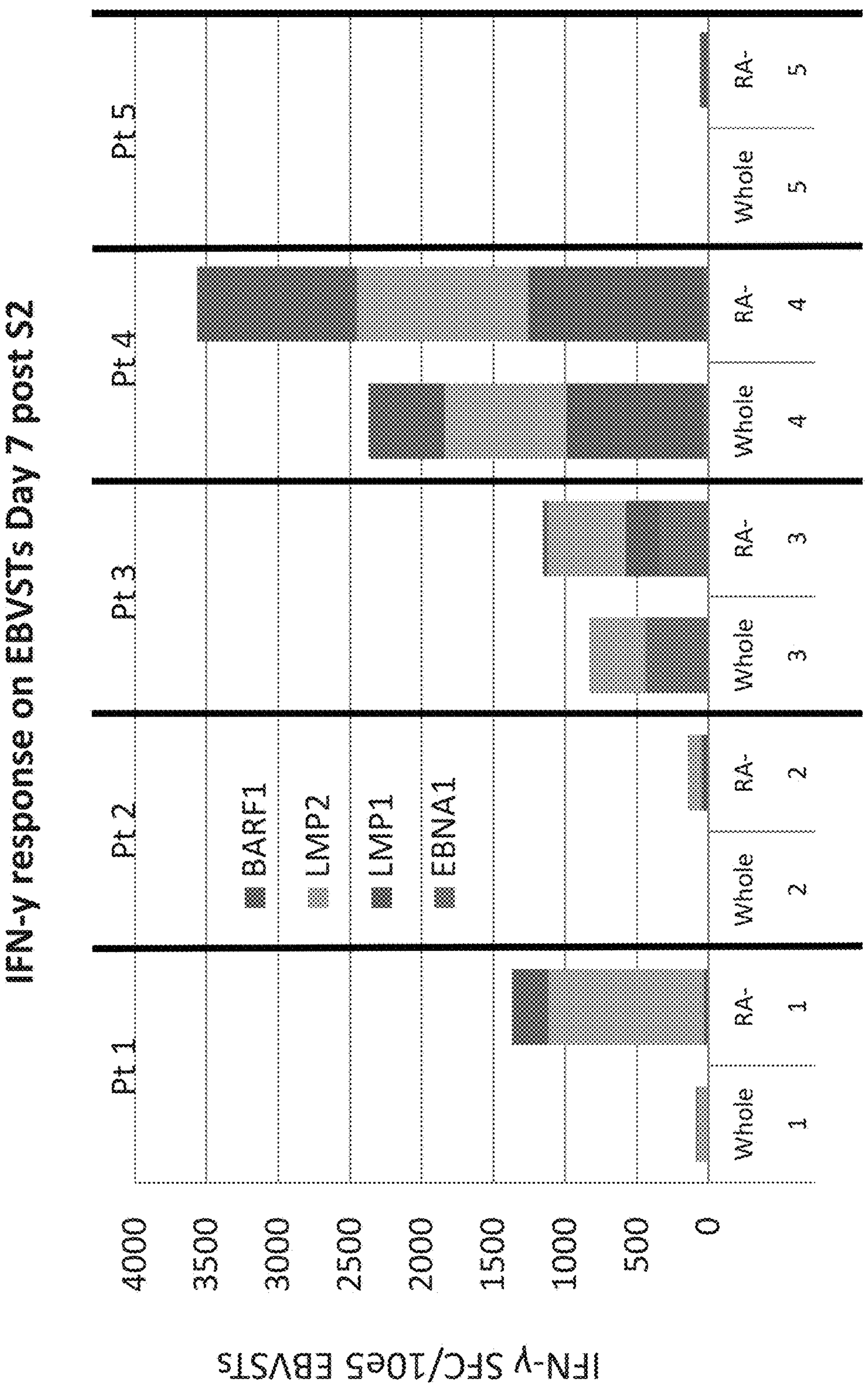
FIG. 16 demonstrates CD45RA depletion increased antigen specificity in EBVSTs from lymphoma patients.
Figure 17:
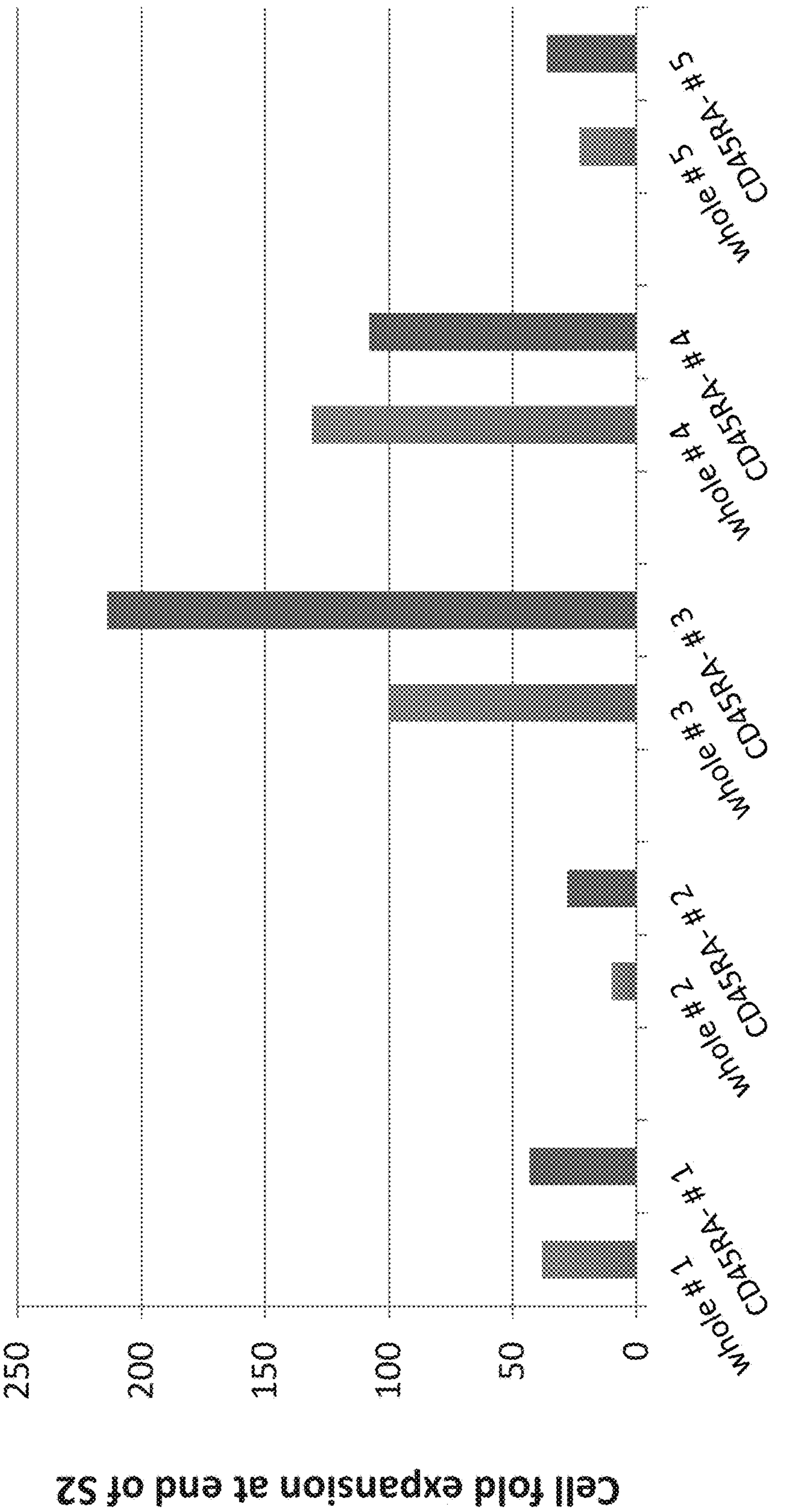
FIG. 17 shows the effect of CD45RA depletion on proliferation of lymphoma patients' EBVSTs.
Figure 18:
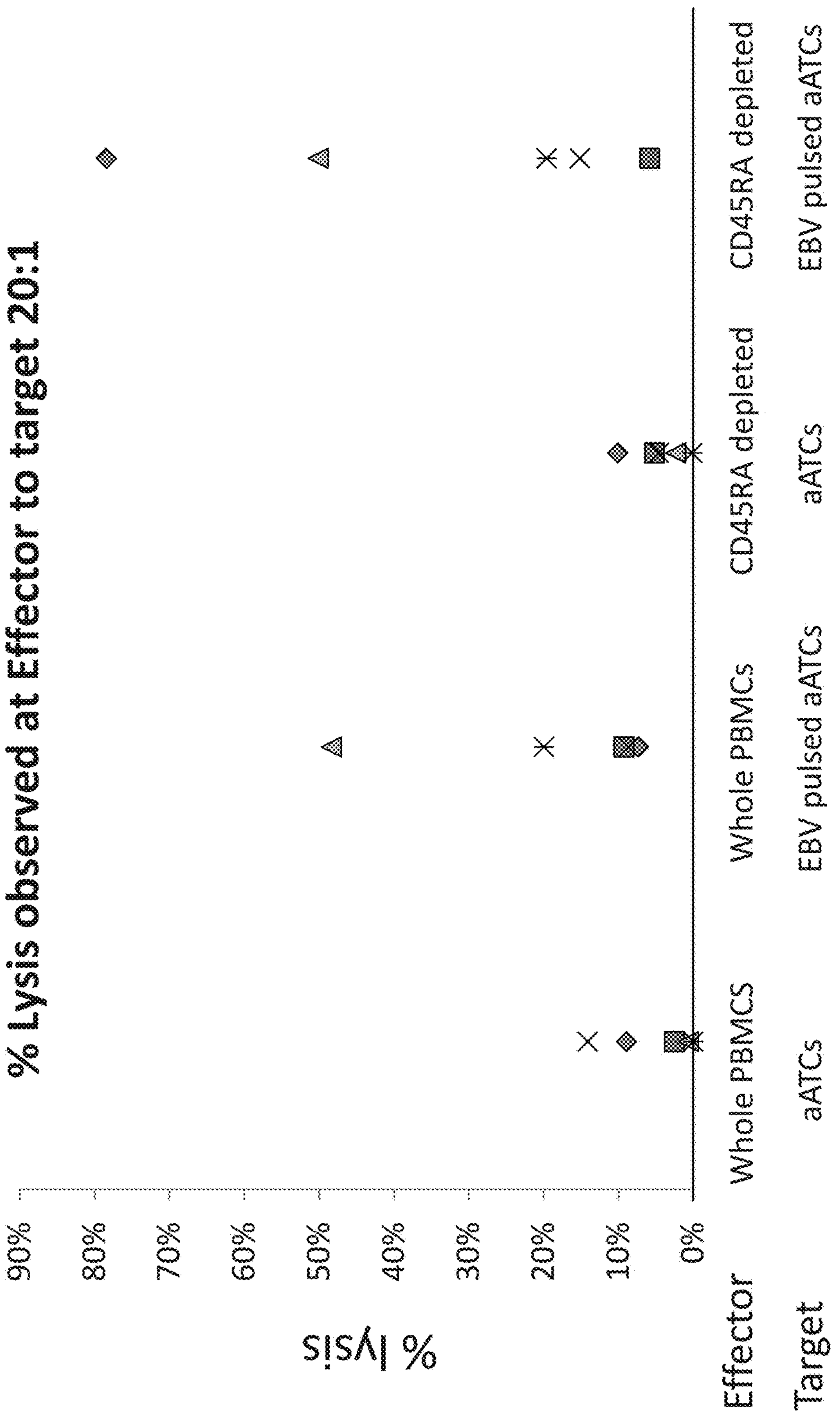
FIG. 18 demonstrates that CD45RA-depletion enhanced cytolytic activity against pepmix-pulsed autologous activated T-cells (aATCs).

The effects of CD45RA depletion was characterized in lymphoma patients, chosen either because their EBVSTs grown without depletion showed high frequencies of NK cells or because they had failed to grow or show antigen-specificity. FIG. 14 shows the total NK cell population at the end of a second stimulation step in five lymphoma patients, demonstrating that CD45RA depletion decreases NK cell population outgrowth in lymphoma patient EBVSTs, and this depletion increased the frequency of the antigen-specific T-cells (illustrated by IFN-γ release ELIspot assay at the end of a second stimulation) (FIG. 15). This experiment was performed in the absence of dendritic cells for the first stimulation. Analogous to results in healthy donors, CD45RA depletion increased antigen specificity in EBVSTs from lymphoma patients (FIG. 16). Proliferation of the lymphoma patients' EBVSTs is demonstrated in FIG. 17. Furthermore, CD45RA depletion enhanced cytolytic activity against pepmix-pulsed autologous activated T-cells (aATCs); percentage lysis was observed at effector to target ratio of 20:1 (FIG. 18).

Figure 19:
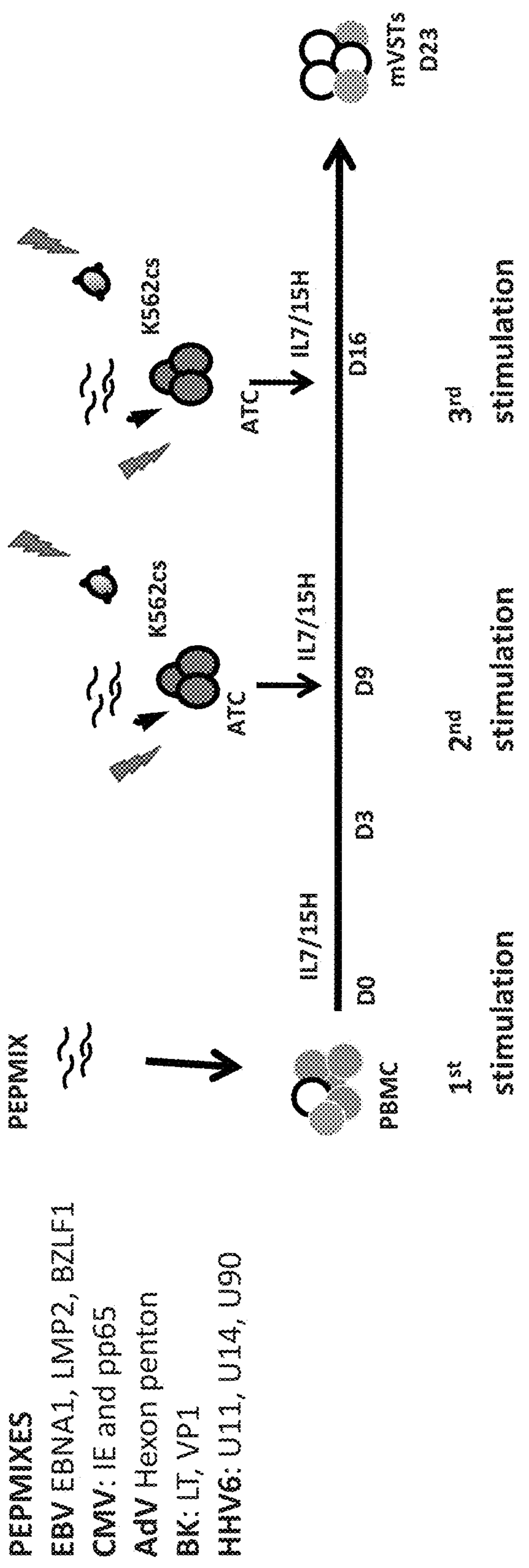
FIG. 19 illustrates an embodiment of generation of T-cells specific for EBV, CMV, Adenovirus, BK virus, and HHV6 (multivirus-specific T-cells).

FIG. 19 illustrates the generation of multivirus-specific T-cells specific for EBV, CMV, Adenovirus, BKG virus, and HHV6. As merely an example, the pepmixes include peptides from EBNA1, LMP2, and BZLF1 for EBV; IE and pp65 for CMV; hexon and penton for Adenovirus, LT and VP1 for BK, and U11, U14, and U90 for HHV6. As illustrated therein, a pepmix comprising peptides that span part or all of each of these viral antigens is exposed to PBMCs at day 0 in the presence of IL7 and high dose IL15. Upon the second stimulation beginning at day 9, pepmix-activated ATCs and costimulatory cells (such as K562cs cells) are exposed to the cells in the presence of IL7 and high dose IL15. At a third stimulation step, such as beginning at day 16, another round of pepmix-activated ATCs and costimulatory cells (such as K562cs cells) are exposed to the cells in the presence of IL7 and IL15H, ultimately producing multivirus (m)VSTs (D23) cells.

Figure 20:
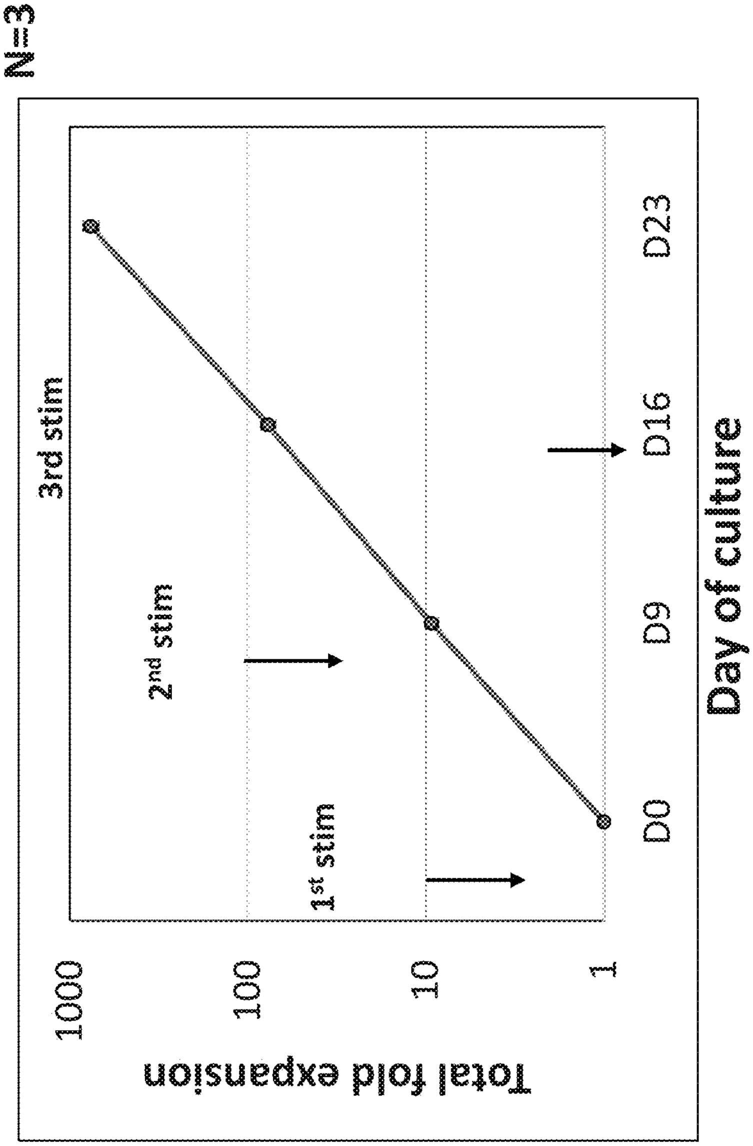
FIG. 20 demonstrates expansion of multivirus-specific T-cells.
Figure 21:
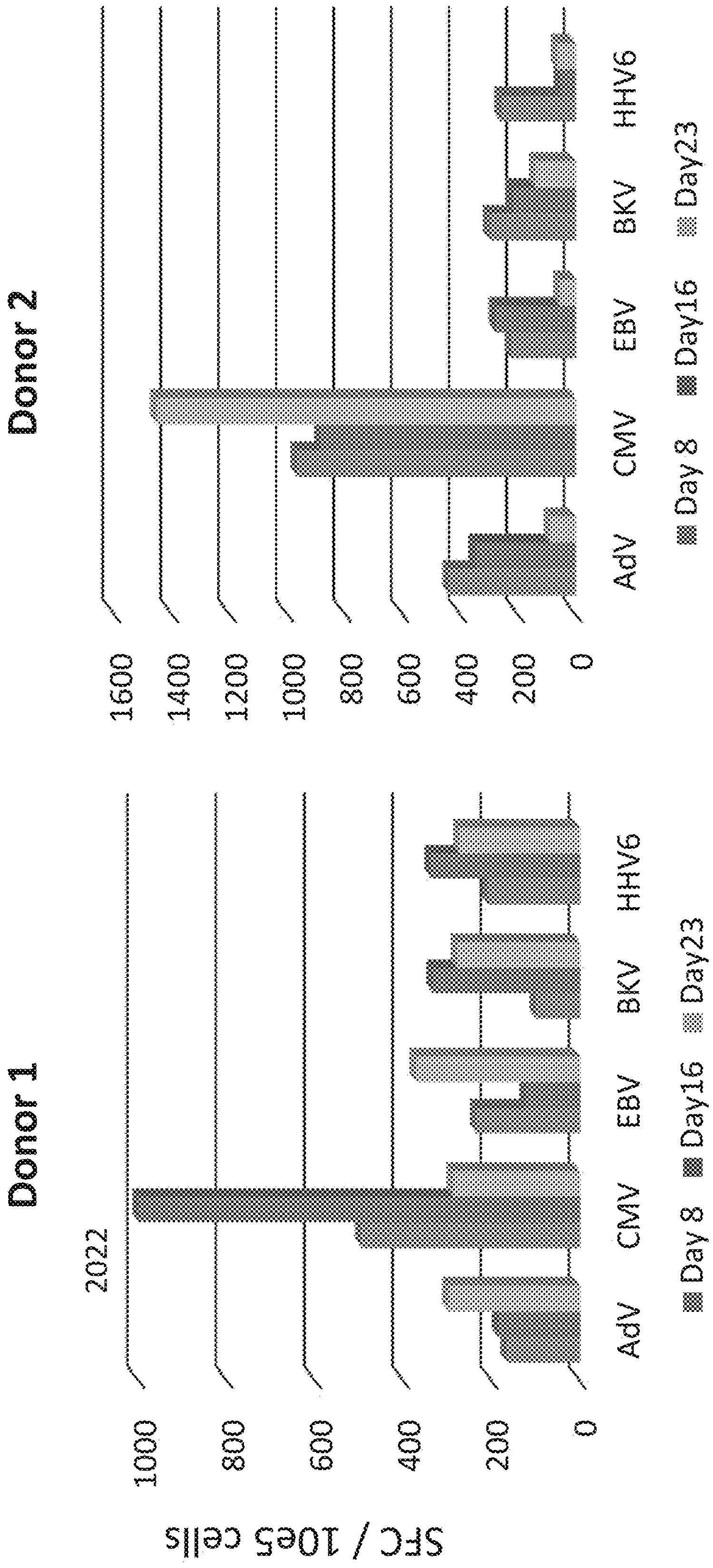
FIG. 21 shows antigen specificity of multivirus-specific T-cells.

FIG. 20 demonstrates the total fold expansion at and after subsequent stimulation steps of embodiments of the method. The antigen specificity of the multivirus-specific T-cells was examined, and T-cells with specificity for all 5 viruses expanded (FIG. 21).

Figure 22:
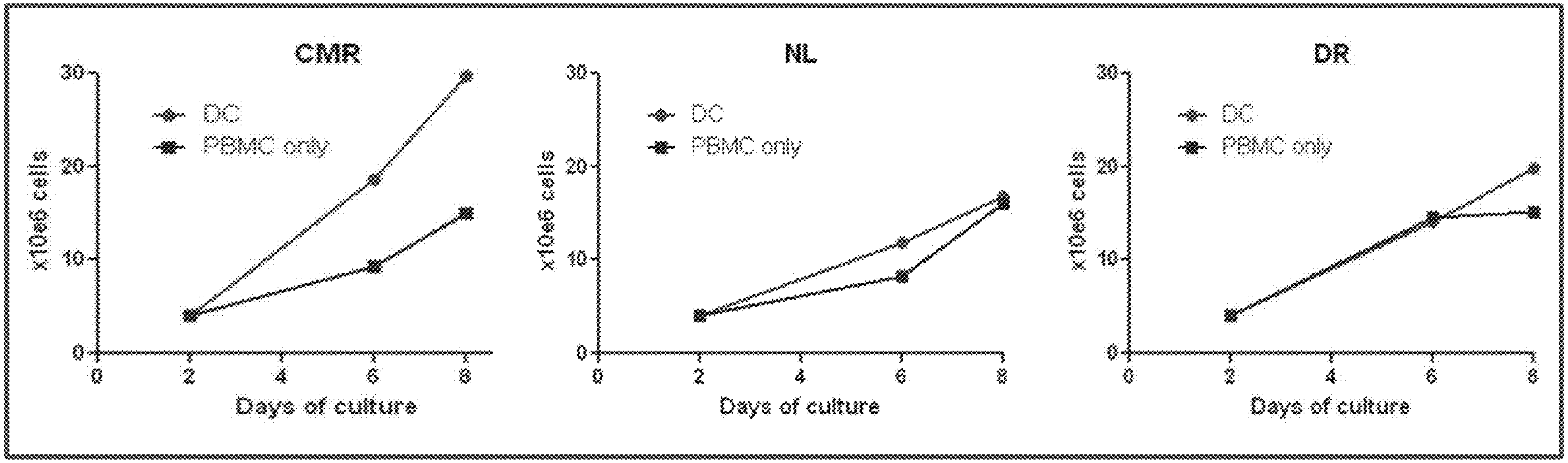
FIG. 22 demonstrates proliferation of VZV-specific VSTs after a first stimulation.
Figure 23:
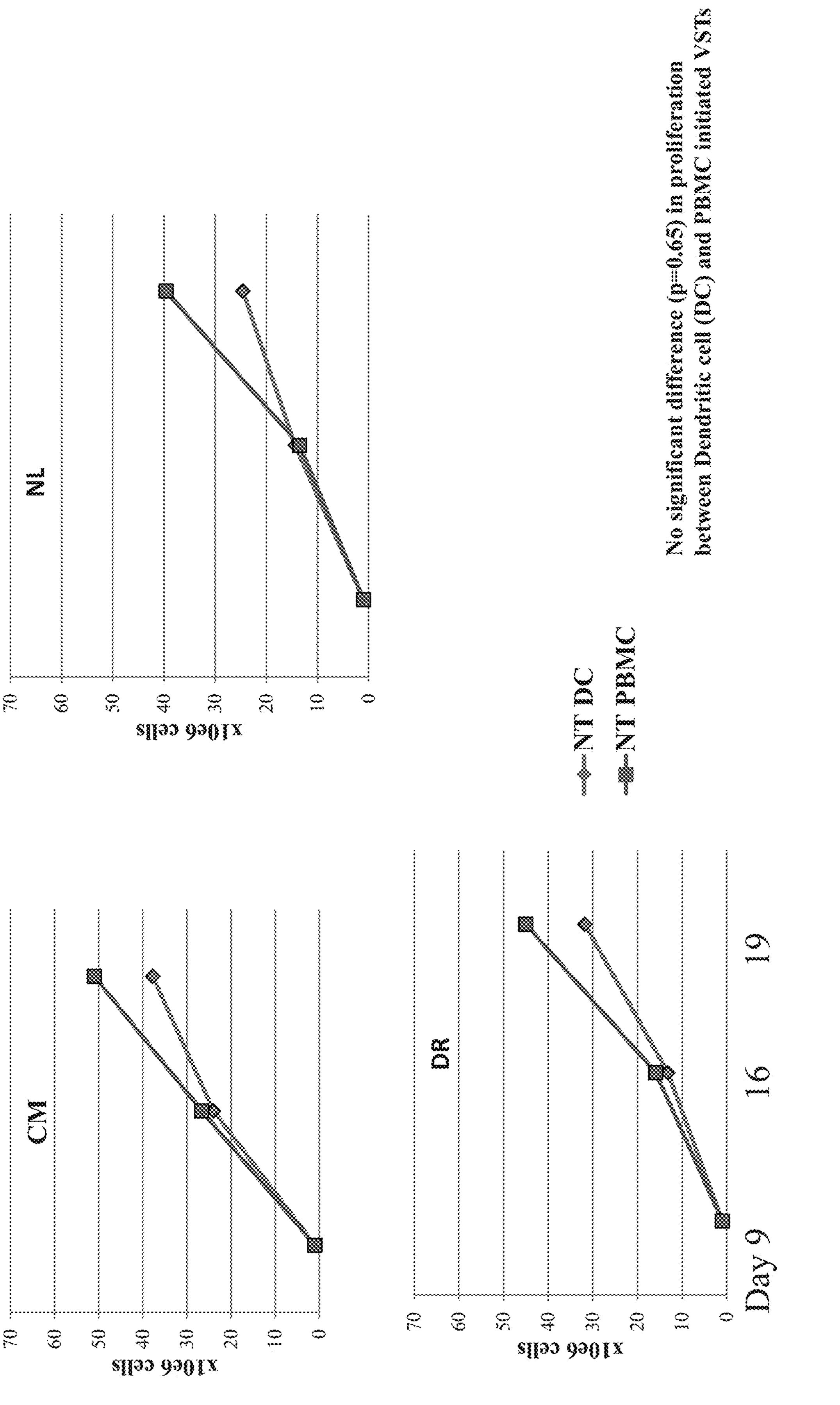
FIG. 23 shows expansion of VZVSTs after a second stimulation.
Figure 24:
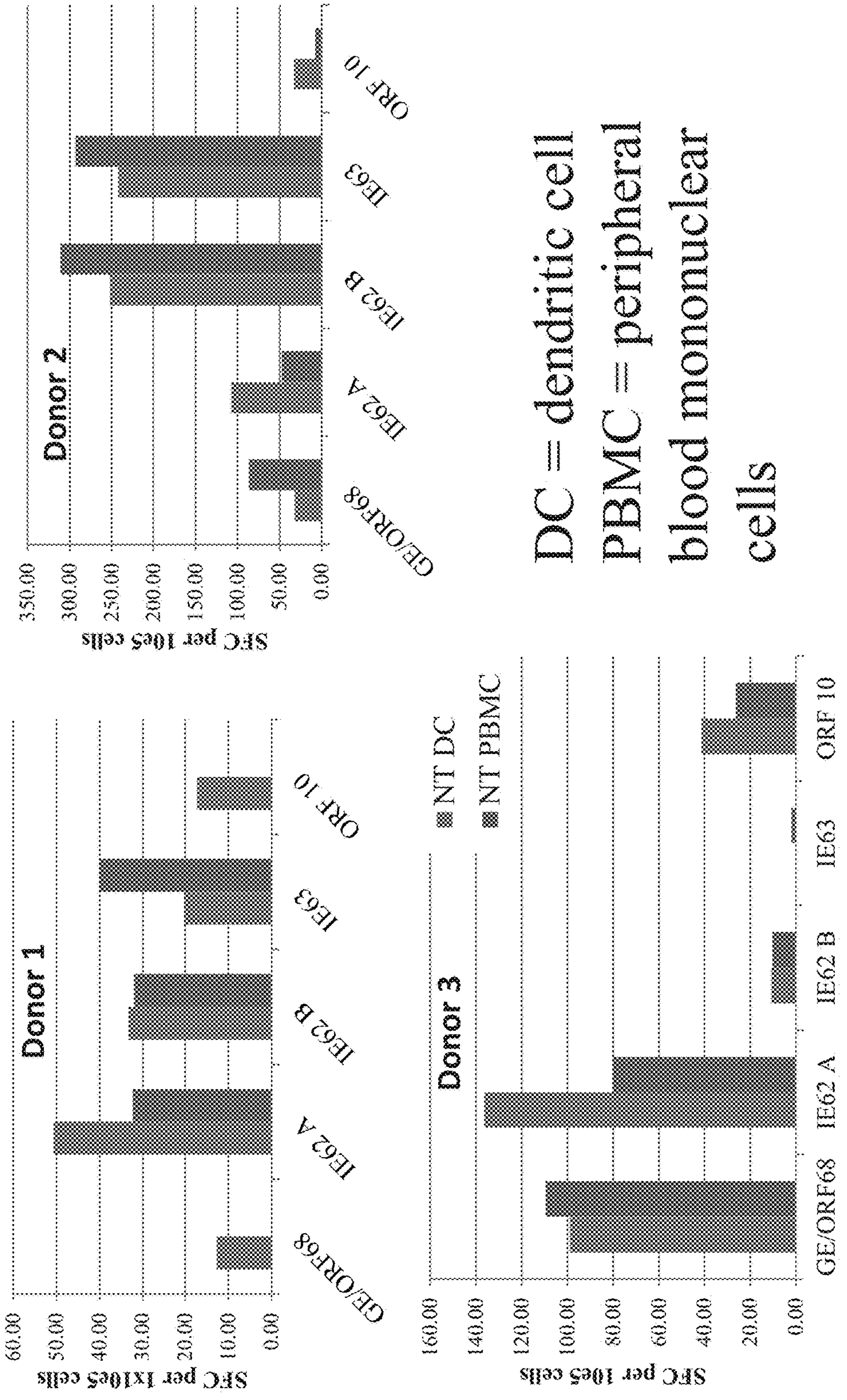
FIG. 24 demonstrates specificity of the VZVSTs after a first stimulation (at day 8).
Figure 25:
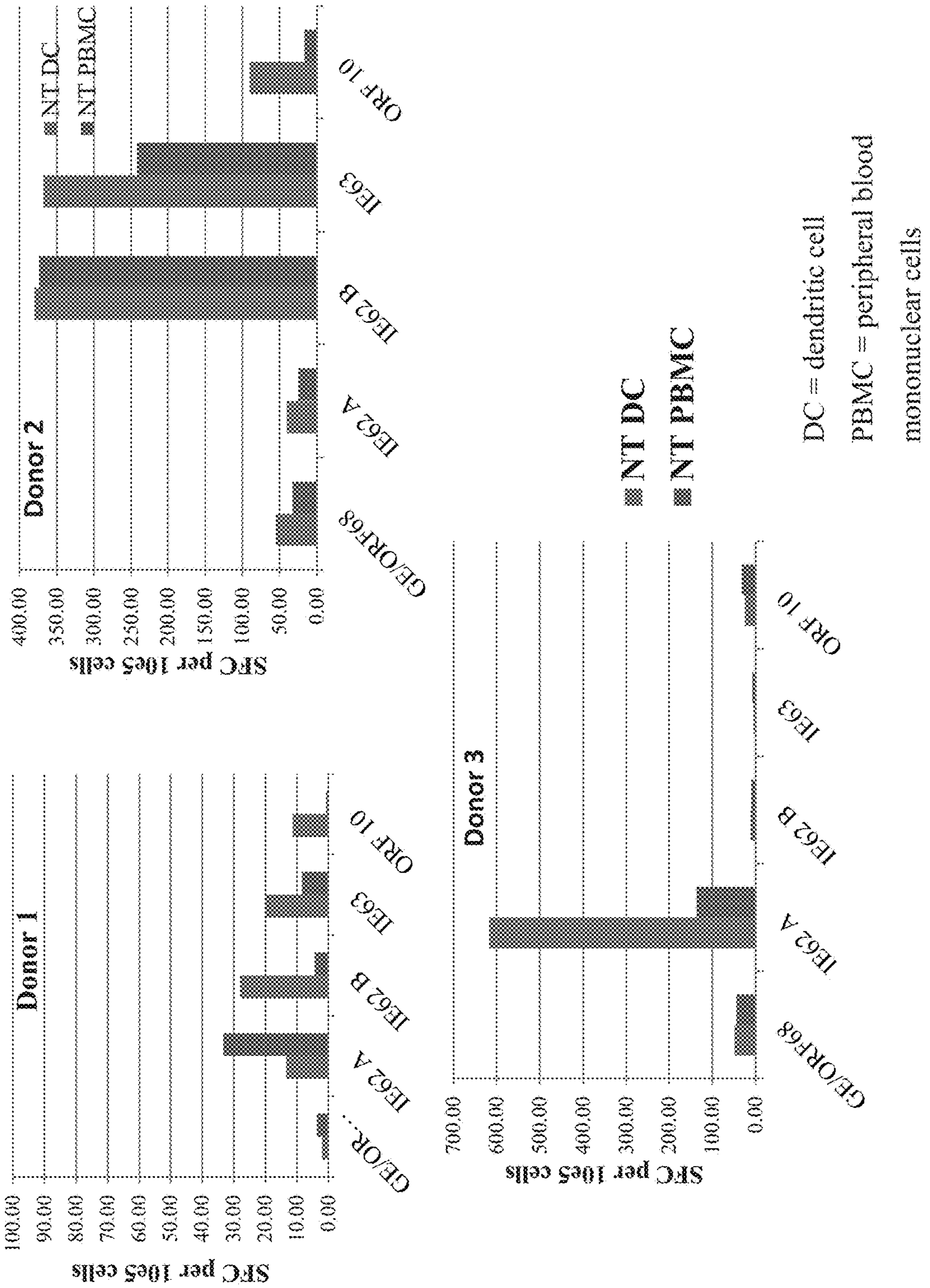
FIG. 25 demonstrates specificity of VZVSTs after a second stimulation (at day 16).

In specific embodiments, CAR-modified T-cells may be generated using methods of the disclosure. FIG. 22 demonstrates proliferation of VZV-specific VSTs after a first stimulation, again comparing methods of the disclosure to those that employ dendritic cells; there was no significant difference in proliferation between DC-initiated VSTs and PBMC-initiated VSTs or in expansion of the VZVSTs after the second stimulation (FIG. 23). FIGS. 24 and 25 demonstrate specificity of the VZV-specific VSTs after a first stimulation at day 8 (FIG. 24) and after a second stimulation at day 16 (FIG. 25). In specific cases, and without being bound by theory, such an outcome is because if the antigens are not expressed in tumor cells they are not anergic.

In summary, in specific demonstrations in the present Example, provided herein is a comparison of EBVSTs expanded with dendritic cells in IL4/7 to methods encompassed herein. As demonstrated, a high dose IL-15 and IL-7 increased the fold expansion of EBVST in healthy donors and patients as well as increased the frequency of EBV-antigen-specific T-cells in both healthy donors and patients, in addition to eliminating the requirement for dendritic cells in first stimulations. The strategy was effective for multiple viruses (EBV, CMV, adenovirus, BK virus, HHV6 and VZV) and was effective for retrovirally-transduced virus-specific T-cells. Finally, demonstrated herein are data to show that CD45RA-depletion leads to broader and higher antigen specificity and decreased NK cell population in EBVSTs, for example.

Example 3

Generation of HIV Antigen-Specific T-Cells

Figure 26:
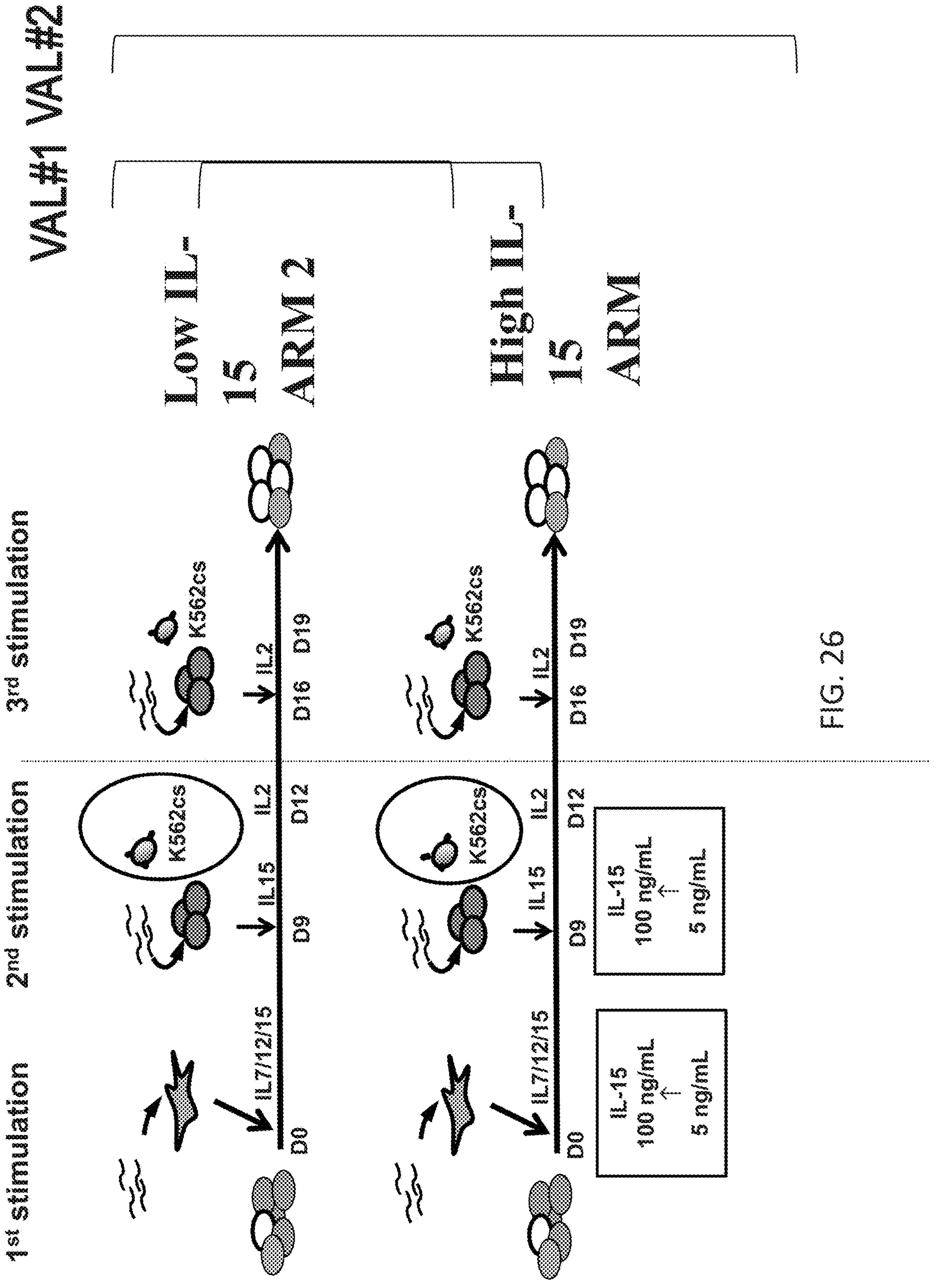
FIG. 26 illustrates manufacturing of HIV-specific T-cells from HIV seropositive donors.
Figure 27:
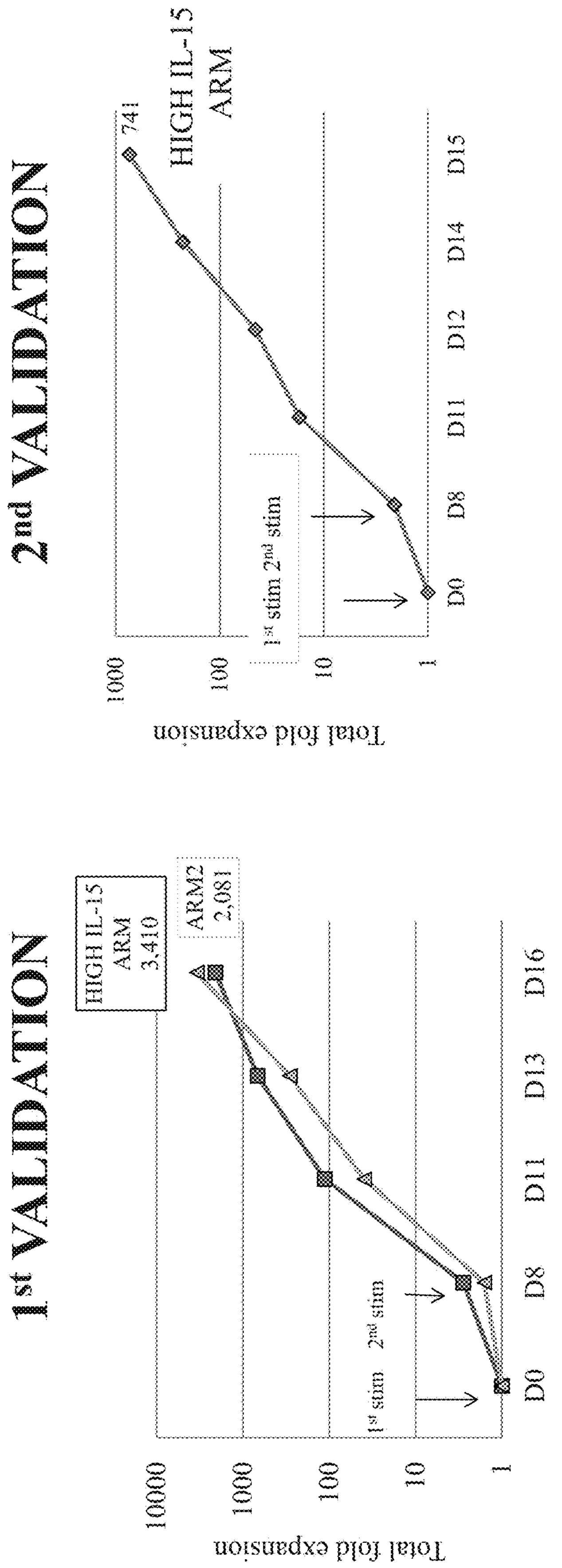
FIG. 27 shows optimal expansion with K562 cells in a second stimulation.
Figure 28:
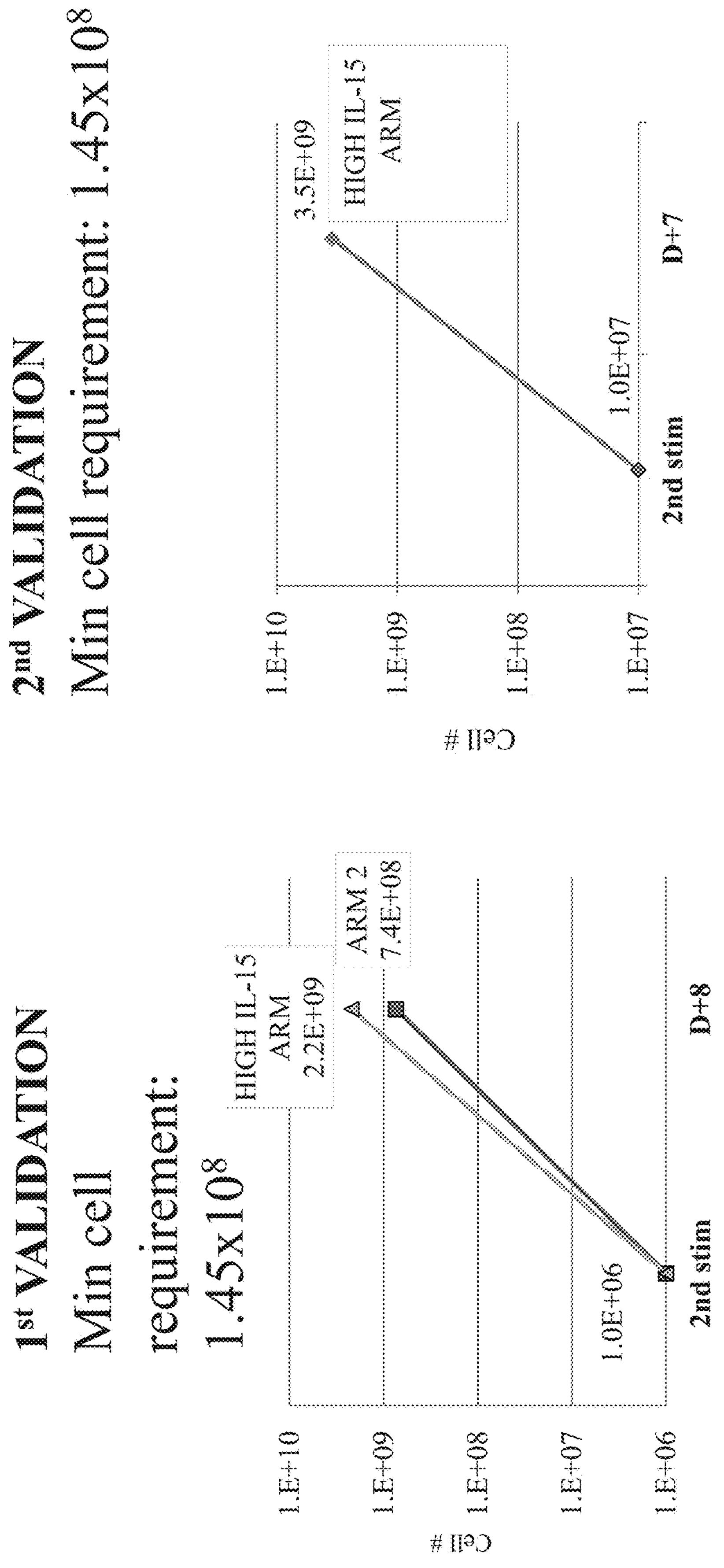
FIG. 28 demonstrates that in the presence of K562, HIV antigen-specific T cells (HIVSTs) expanded to clinically relevant numbers after only two stimulations.

In one embodiment, T cells specific for HIV antigen are produced with methods of the disclosure. FIG. 26 illustrates one embodiment of manufacturing of HIV-specific T cells from HIV seropositive donors. FIG. 27 shows optimal expansion of the cells with K562 cells in a second stimulation. Therein, results are shown after only 2 stimulations (15-16 days)+1 week for DCs. Expansion in presence of K562 is higher than without K562 during the second stimulation. FIG. 28 demonstrates that in the presence of K562, HIV antigen-specific T cells (HIVSTs) expanded to clinically relevant numbers after only 2 stimulations.

Figure 29:
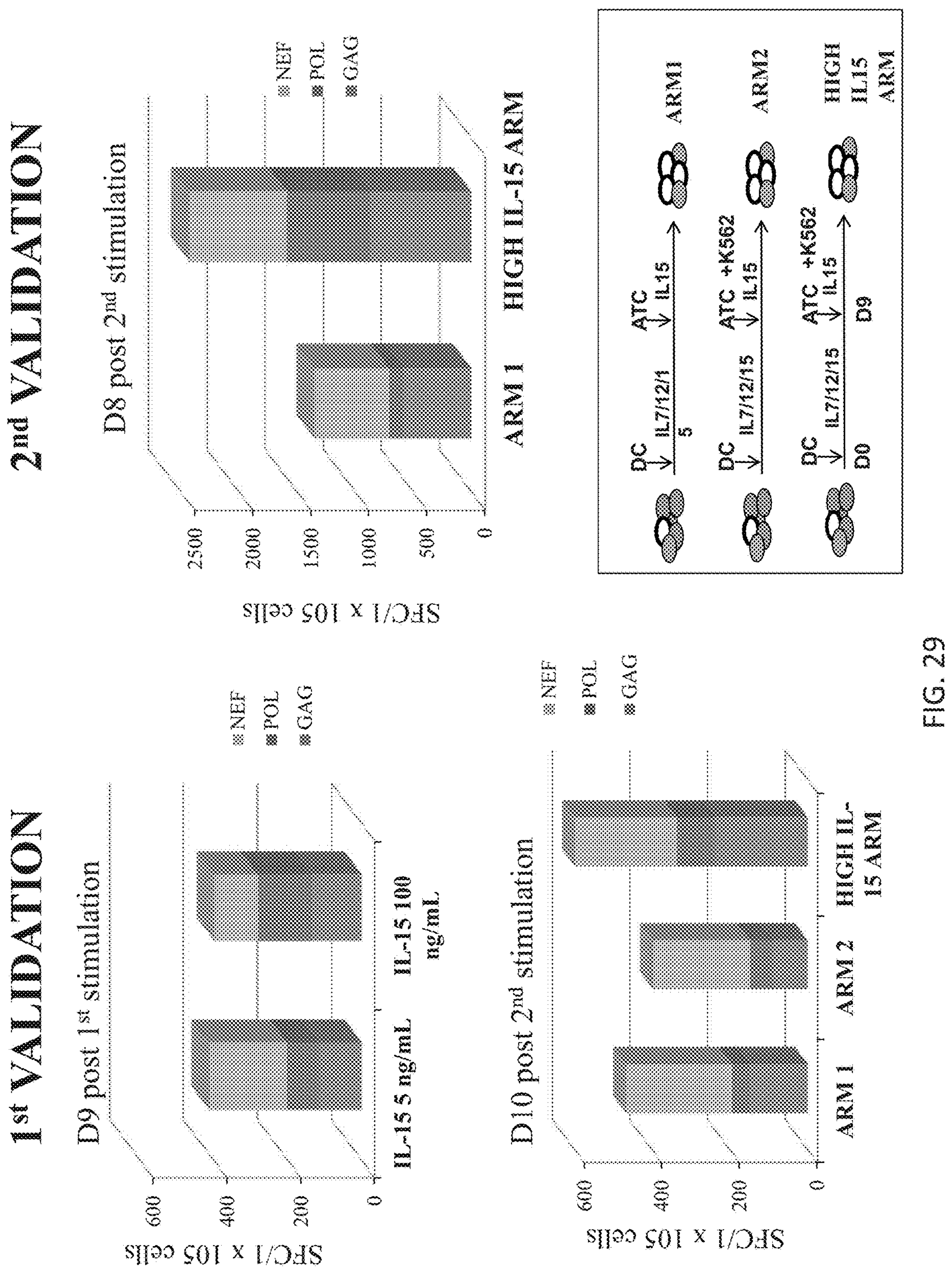
FIG. 29 shows that HIVSTs are specific for multiple HIV antigens.

FIG. 29 shows that HIVSTs are specific for multiple HIV antigens. The specificity of HIVSTs was assessed by interferon (IFN)-γ secretion in response to individual pepmixes for each HIV antigen in an ELIspot assay. The specificity of HIVSTs was assessed by interferon (IFN)-γ secretion in response to individual PepMixes for each HIV antigen in ELIspot assay. All of the lines were multispecific for all 3 antigens. In the first validation, equivalent antigen specificity was observed post first stimulation. Specificity was not lost by adding K562 during a second stimulation. There was an advantage for High dose IL-15 by the end of the second stimulation. For the second validation, there was high background after the first stimulation. Greater specificity was observed for GAG, POL and NEF in ARM2 (High IL-15) than in ARM1 (low IL-15). A negative control included <10 spots per 1e5 HIVSTs.

Figure 30:
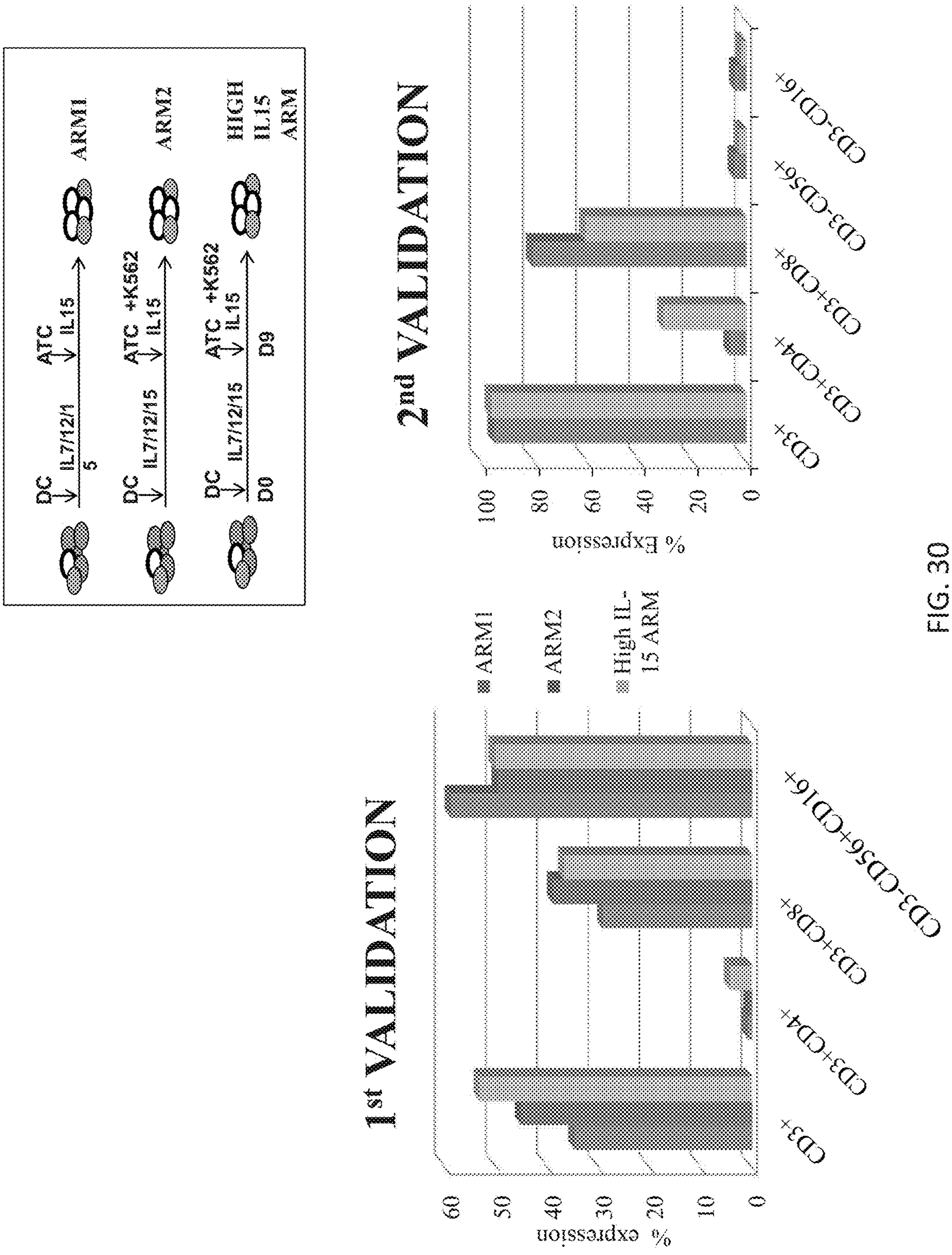
FIG. 30 demonstrates that HIVSTs comprise mixed CD4+ and CD8+ T cells.

FIG. 30 shows that HIVSTs comprise mixed CD4+ and CD8+ T cells. The lines were predominantly CD3+CD8+ T cells, although there were a proportion of CD4+ T cells. The T cell lines contained a subpopulation of CD3−CD56+NK cells. In the first validation, there was a similar phenotype with more CD3-CD56+CD16+NK cells and fewer CD3+ T-cells in ARM1. In the second validation, there was a higher ratio of CD4+ to CD8+ cells in ARM2 (High IL-15) (more balanced and few NK Cells). Because CD4 T cells are known to provide CD8 T cell help, aiding in memory, persistence, and effector functions, it is critical that any T cell immunotherapy approach for HIV utilizes CD4 T cells. While the infusion of a small percentage of CD4 T cells may seem counterintuitive, non-CD4−depleted T cells have been infused in the past, and no significant increase in viral load was observed.

Figure 31:
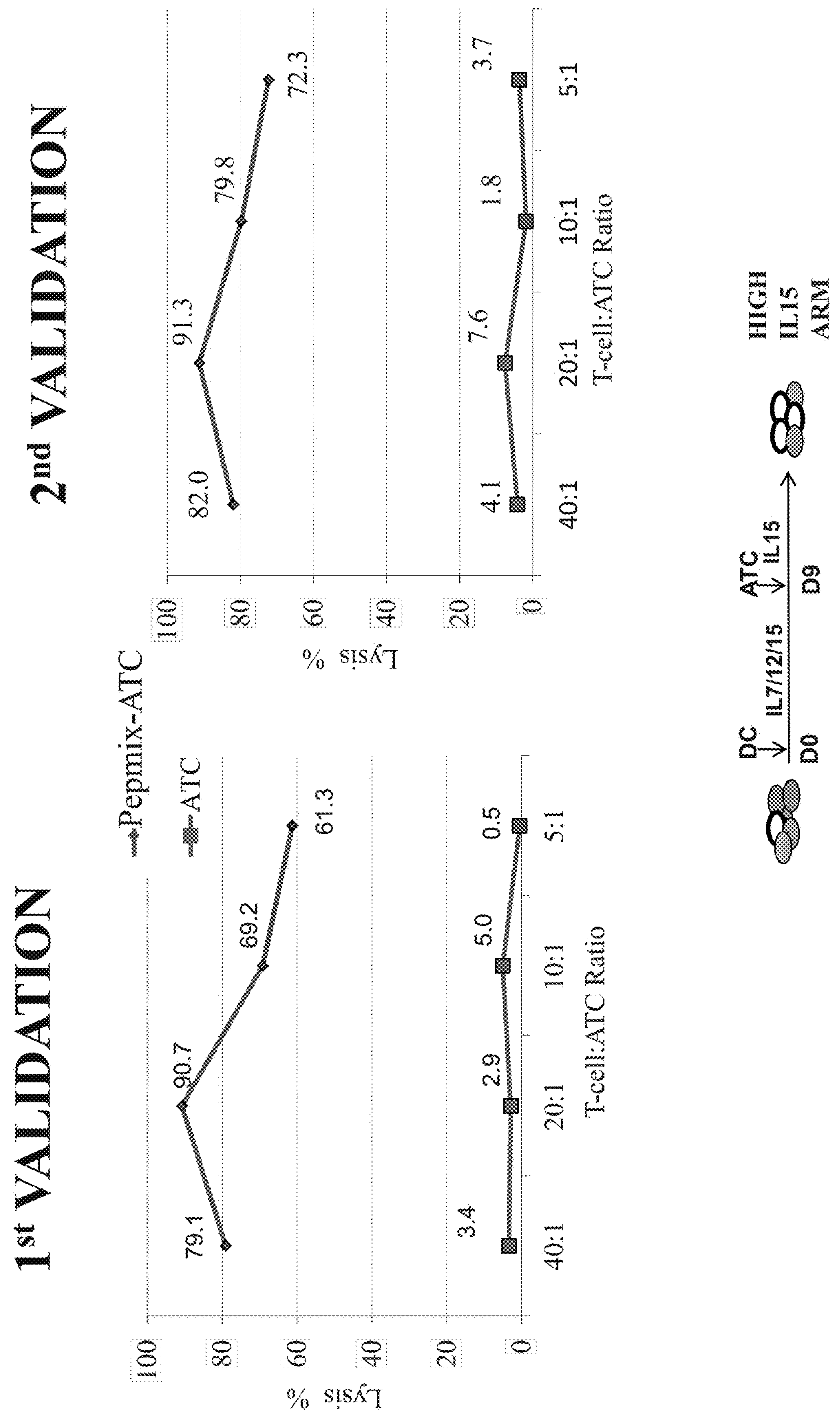
FIG. 31 demonstrate that HIVSTs can lyse antigen-pulsed and HIV-infected targets.

FIG. 31 demonstrates that HIVSTs can lyse antigen-pulsed and HIV-infected targets. To evaluate the cytolytic specificity of the HIVSTs, the inventors incubated the HIVSTs with a panel of $^{51}$Chromium ($^{51}$Cr)-labeled autologous pepmix-ATCs target cells. Importantly, HIVSTs were specific because lysis of activated autologous target cells alone was not observed. The ability of HIVSTs to lyse antigen-expressing targets was measured using an 4-hour $^{51}$Chromium-release assay. Target cells consisted of autologous PHA-blasts that were pulsed with either media or Gag, Pol, or Nef PepMixes and were loaded with chromium. HIVSTs were cultured with target cells pulsed with only the antigens they were specific for, which was predetermined by IFN-γ ELIspot assay.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of producing Epstein Barr Virus (EBV)-specific T cells, the method comprising:
   (a) culturing peripheral blood mononuclear cells (PBMCs) depleted of CD45RA-positive cells with a library of peptides comprising peptides corresponding to at least part of the amino acid sequence of one or more EBV antigens, in the presence of IL-7 and IL-15, and in the absence of exogenously added IL-4 and IL-2, and
   (b) modifying an EBV-specific T cell obtained at step (a) to express a chimeric antigen receptor (CAR) to produce EBV-specific T cells expressing a CAR.

2. The method according to claim 1, wherein the one or more EBV antigens include an EBV antigen selected from the group consisting of: LMP1, LMP2, EBNA1, BARF1, BZLF1, BRLF1 and BMLF1.

3. The method according to claim 1, wherein the library of peptides comprises peptides corresponding to at least part of the amino acid sequence of each of LMP1, LMP2, EBNA1, BARF1, BZLF1, BRLF1 and BMLF1.

4. The method according to claim 1, wherein the library of peptides comprises peptides have a length of between 8 and 20 amino acids, and comprises peptides overlapping in sequence by between 6 and 16 amino acids, optionally wherein the library of peptides comprises peptides have a length of 15 amino acids, and comprises peptides overlapping in sequence by 11 amino acids.

5. The method according to claim 1, wherein the method comprises stimulation in the presence of 5 to 15 ng/ml IL-7, optionally wherein the method comprises stimulation in the presence of about 10 ng/ml IL-7.

6. The method according to claim 1, wherein the method comprises stimulation in the presence of 5 to 15 ng/ml IL-15, optionally wherein the method comprises stimulation in the presence of about 10 ng/ml IL-15.

7. The method according to claim 1, wherein producing EBV-specific T cells further comprises a preceding step of: depleting a population of PBMCs of CD45RA-positive cells to obtain PBMCs depleted of CD45RA-positive cells.

8. The method according to claim 1, wherein modifying an EBV-specific T cell to express a CAR comprises transducing an EBV-specific T cell with a retroviral vector encoding a CAR.

9. The method according to claim 1, wherein the method further comprises:
   (c) culturing the EBV-specific T cells expressing a CAR in the presence of irradiated human leukocyte antigen (HLA)-negative lymphoblastoid cells.

10. The method according to claim 1, wherein the CAR targets a cancer antigen.

11. The method according to claim 1, wherein the CAR targets CD30.

* * * * *